US005819741A

United States Patent [19]
Karlsson et al.

[11] Patent Number: 5,819,741
[45] Date of Patent: *Oct. 13, 1998

[54] CARDIAC MONITORING SYSTEM AND METHOD

[75] Inventors: Per Karlsson, Taby; Gunilla Lundahl, Lidingo; Michael Oljemark, Saltsjo-Boo; Johan Ubby, Vaxholm, all of Sweden

[73] Assignee: Ortivus Medical AB, Taby, Sweden

[*] Notice: The term of this patent shall not extend beyond the expiration date of Pat. No. 5,520,191.

[21] Appl. No.: 653,448

[22] Filed: May 24, 1996

Related U.S. Application Data

[63] Continuation-in-part of Ser. No. 320,511, Oct. 7, 1994, Pat. No. 5,520,191.

[51] Int. Cl.⁶ .................................................. A61B 5/0402
[52] U.S. Cl. ........................................................... 128/710
[58] Field of Search .................................. 128/696, 710, 128/731; 364/413.06

[56] References Cited

U.S. PATENT DOCUMENTS

| | | | |
|---|---|---|---|
| 3,548,813 | 12/1970 | Berner | 235/151.3 |
| 3,858,034 | 12/1974 | Anderson | 128/2.06 |
| 4,213,465 | 7/1980 | Renheim | 128/731 |
| 4,570,225 | 2/1986 | Lundy | 364/417 |
| 4,850,370 | 7/1989 | Dower | 128/699 |
| 4,924,875 | 5/1990 | Chamoun | 128/696 |
| 5,038,800 | 8/1991 | Oha | 128/904 |
| 5,410,473 | 4/1995 | Kaneko et al. | 364/413.06 |
| 5,469,857 | 11/1995 | Laurent et al. | 128/710 |
| 5,520,191 | 5/1996 | Karlsson et al. | 128/702 |

OTHER PUBLICATIONS

High Resolution ECG System for Micropotential Analysis and Shape Classification, Rix et al., Annual International Conference of the IEEE Engineering in Medicine and Biology Society, Vol. 13, No. 2 (1991).

*Primary Examiner*—Scott M. Getzow
*Attorney, Agent, or Firm*—Cooper & Dunham LLP

[57] ABSTRACT

A cardiac monitoring method and system provides advanced ischemia and infarction analysis and monitoring. Advanced calculations are performed on ECG signals to obtain parameter values relating to myocardial ischemia and infarction. Dominant heart beats are averaged to form a smooth beat, which is analyzed to determine the parameter values continuously and in real-time. The result of each analyzed time interval is presented as points in a trend graph on a monitoring display. All calculations are performed on-line and the trend curves are updated immediately. Systems and methods for monitoring, analyzing, and/or diagnosing cardiac activity that display a state of signals received from leads attached to a patient on a graphic depiction of the patient are also provided. The graphic depiction of the patient may include electrode position information.

21 Claims, 19 Drawing Sheets

4 ELECTRODES
(ALL EXCEPT V LEAD)

HOLTER

CARDIAC MONITORING SYSTEM AND METHOD

This application is a continuation-in-part application of U.S. Ser. No. 08/320,511, filed Oct. 7, 1994 now U.S. Pat. No. 5,520,191.

BACKGROUND OF THE INVENTION

(1) Field of the Invention

The present invention relates to cardiac monitoring systems and, more particularly, to cardiac monitoring systems which provide an analysis and display of parameters relating to the condition of ischemic patients. The invention also relates to systems and methods for monitoring, analyzing, diagnosing, and/or receiving radiotransmissions relating to cardiac activity and displaying a state of signals received from leads attached to a patient on a graphic depiction of the patient.

(2) Description of the Related Art

A number of new clog dissolving agents presented by the pharmaceutical industry during the past couple of years have given cardiologists the ability to immediately treat acute myocardial ischemia through chemical thrombolytic therapy. However, it is frequently difficult to properly control and adjust such therapy during the acute phase of a myocardial ischemia. Known methods are either expensive or have too large a delay (up to several hours) between the time of the myocardial ischemia time and the presentation of the results. Some cardiac monitoring systems and methods also utilize a known 12-lead ECG in which ECG signals are displayed directly on a monitor in real-time. Such a 12-lead ECG arrangement has the disadvantages that a large number of electrodes must be placed on the patient in positions which cover mainly the frontal parts of the myocardium. A large storage capacity is also required in order to record all the ECG signals from the electrodes. However, many doctors are familiar with the format of the 12-lead ECG.

SUMMARY OF THE INVENTION

The present invention constitutes a substantial improvement in cardiac monitoring systems, and in particular, an improvement in cardiac monitoring systems providing an analysis and display of parameters relating to the condition of ischemic patients. It is an object of the present invention to overcome the aforementioned disadvantages of known cardiac monitoring systems. In particular, it is an object of the present invention to provide real time parameters describing the acute condition of the myocardium during thrombolytic therapy in the initial phase of myocardial infarctions.

Further, it is an object of the present invention to provide a cardiac monitoring system in which the ECG signals are represented by three perpendicular leads which are continuously averaged and stored in equal intervals and then later displayed in the format of a derived standard 12-lead ECG.

It is also an object of the invention to continuously store the three perpendicular leads, X, Y and Z, and recalculate the signals therefrom in order display a derived standard 12-lead ECG in real-time.

It is also an object of the invention to provide an improved method to be used in pharmaceutical studies to verify the actual benefits of new drugs.

It is a further object of the invention to provide an improved monitoring method to be used during different kinds of coronary operations, such as PTCA—coronary artery balloon dilatation, or other procedures requiring an accurate real-time analysis and monitoring.

It is a further object of the invention to provide cardiac monitoring systems and methods that display a state of signals received from leads attached to a patient on a graphic depiction of the patient.

The method in a preferred embodiment of the present invention presents the required information in real-time using advanced calculations on ECG signals to obtain "simple" parameter values describing the myocardial ischemia (lack of oxygen) and the course of infarction. Eight standard ECG surface electrodes are placed on the patient according to the Frank electrode system developed in the 1940s. The signals in the eight leads are processed in a known manner to form the ECG vector which can be described by three perpendicular leads: X, Y, and Z. These three leads contain all the information necessary to describe the ECG completely.

ECG changes are continuously analyzed to reflect the course of ischemia and infarction based on vectorcardiography. All dominant beats are continuously acquired for the analysis and averaged at even intervals to form one very smooth beat, suitable for high definition calculations. Those intervals may range from ten seconds up to four minutes. The first averaged beat is used as an initial reference beat. All succeeding, averaged beats will be compared to this initial beat to plot the changes.

The resulting, averaged beat is analyzed to form a plurality of parameters. The ST vector magnitude (ST-VM) measures the offset of the ST-segment and is commonly accepted as a measure of ischemia in the myocardium. The change of the ST magnitude compared to the initial reference beat (when monitoring was started) (STC-VM) is also calculated. The QRS vector difference (QRS-VD) measures changes in the QRS complex compared to the initial ECG and reflects the change in morphology of the QRS complex compared to when monitoring was started. The QRS-VD parameter has been linked to the course of the myocardial infarction in several studies.

The invention displays the result of the advanced analysis from every time interval as a new point in very simple trend graphs that are continuously updated. All calculations are performed online so the trend curves are updated immediately. The fundamental advantage of this method is that every complex and subtle information from the ECG signals is analyzed and processed to finally form simple parameter values which are displayed in simple trends. Since the result is presented in the simple graphical form of a trend over time, it is perfect for on-line monitoring and the trend curves provide immediate information on the degree of ischemia or the course of an ischemia. A change in the condition of the heart may even be visible on the display before the patient undergoes pain.

Since the average ECG is always stored, the original ECG of every point of the trend curve may always be displayed as either a derived 12-lead ECG, the X, Y and Z leads, vector magnitude or vector loops. When a patient is monitored, the acquired information is permanently stored in the central workstation of the system. The information may be copied onto recording media, such as a 3.5" floppy disk, and subsequently analyzed for clinical or scientific purposes.

DETAILED DESCRIPTION OF THE PREFERRED EMBODIMENTS

Figure 7:
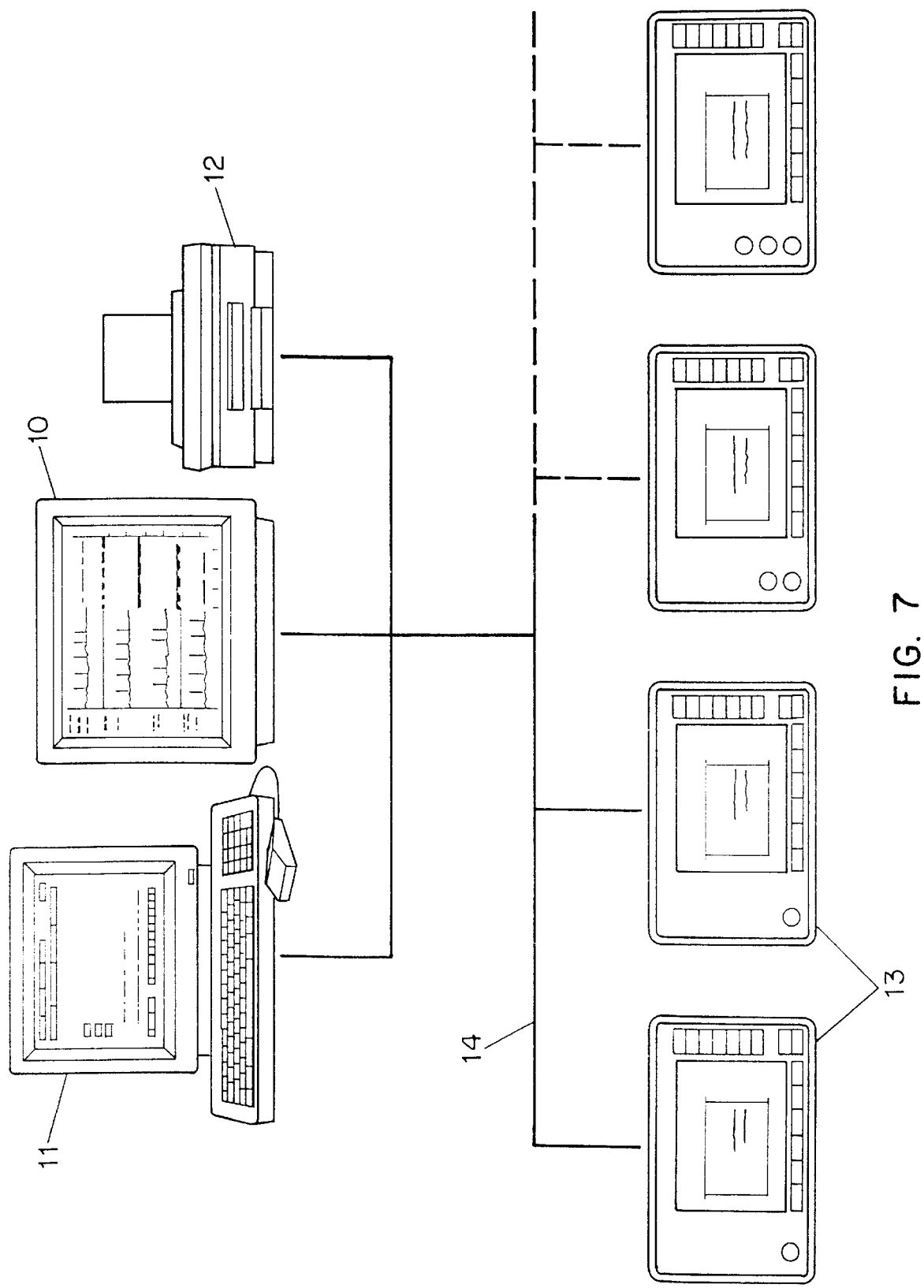
FIG. 7 is a diagram illustrating elements of the system in a first embodiment of the invention.

FIG. 7 shows the setup of the system in a first embodiment of a system utilizing the invention. It consists of at least one central monitoring unit 10, a central workstation 11 for controlling the system, including the display on the central monitoring unit(s), and for storing data, a laser printer 12 and a plurality of bedside monitors 13, one for each patient. All of the units communicate via an Ethernet network 14.

Processing functions are divided between central workstation 11 and each bedside monitor 13. The distributed intelligence ensures maximum system reliability and offers both powerful traditional monitoring and advanced ischemia monitoring.

Figure 12:
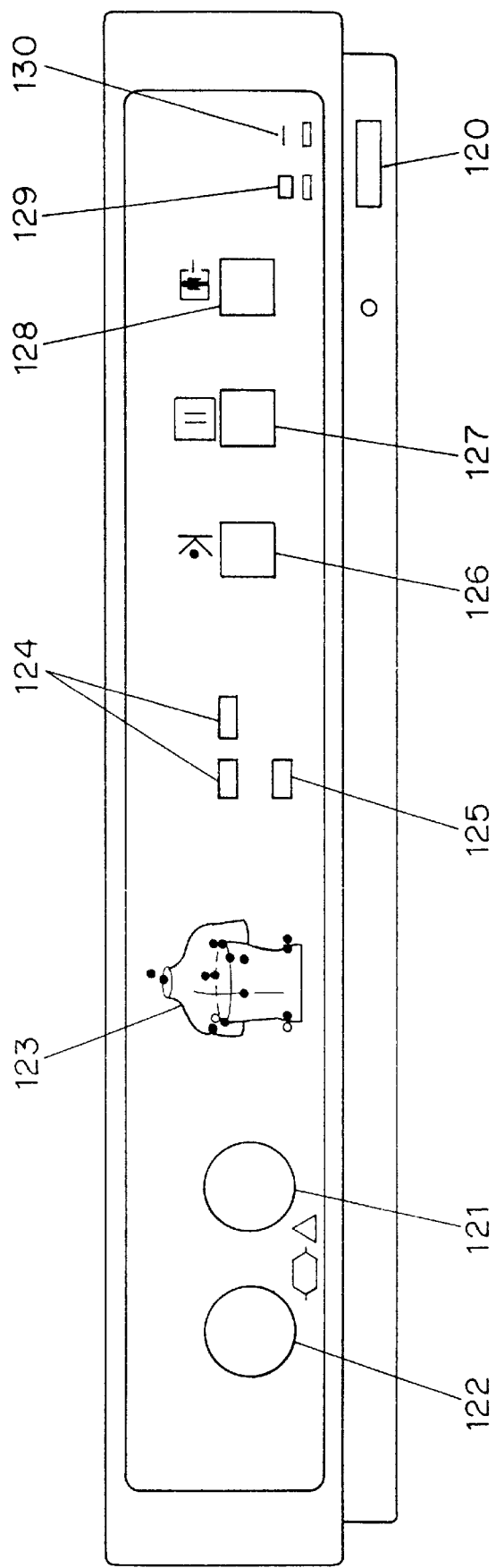
FIG. 12 shows the front face of an acquisition module used in another embodiment of a system employing the invention.

Each of the bedside monitors 13 combines multilead arrhythmia analysis with new, advanced ischemia monitoring features and does all the calculations for the ECG analysis, presents the information on the display and transmits it over Ethernet network 14 to a central processing unit in the workstation 11. FIG. 12 shows the front face of an exemplary bedside monitor 13. In addition to the ECG analysis, each bedside monitor 13 is also available with a number of options, such as non-invasive blood pressure, pulse oximetry, dual invasive pressures and dual temperatures, and is operated simply by touching the self-instructive menus on the front of the monitor. Analogue ECG outputs on the back of the bedside 15 monitors allow connection to other medical equipment.

Eight ECG leads are used for improved sensitivity of the analysis of both arrhythmias and ischemia. With information from all eight leads, the ischemia analysis is able to reflect ischemic changes from the entire myocardium. The ischemic evolution over time is presented in a trend graph that is continuously updated on the display. The trend graph may include up to 8 days of continuous monitoring. With four traces and a trend graph, a waveform may be displayed for every physiological parameter in addition to the vital trend graphs. (For patients without ischemic symptoms, 4 leads can be used for monitoring.) The averaged beats in the form of the X, Y and Z leads are automatically calculated and stored every minute. From these signals a derived 12-lead ECG may be reviewed on the bedside monitor at any time during the monitoring session.

The central workstation can automatically identify up to six different functions (MIDA, HR/PVC, $spo^2$, NIBP, IBP and Temp for example) in each bedside monitor and all of the physiological information acquired by the bedside monitors can be transferred for examination and storage at the workstation. The monitoring functions controllable by the central workstation will thus vary depending on the configuration of the bedside monitors connected to the central workstation. For example, central workstation 11 may provide conventional ECG monitoring, arrhythmia monitoring, ischemia monitoring with parameters reflecting the ECG changes in clear trend graphs, averaged derived 12-lead ECG display, 24-hour full disclosure arrhythmia of all monitored patients, 24-hour continuous 12-lead ECG display derived from the continuously stored X, Y, and Z leads for all monitored patients and monitoring of any and all non-ECG functions monitored on the bedside monitors such as $spo^2$, NIBP, BP and Temp.

Figure 8:
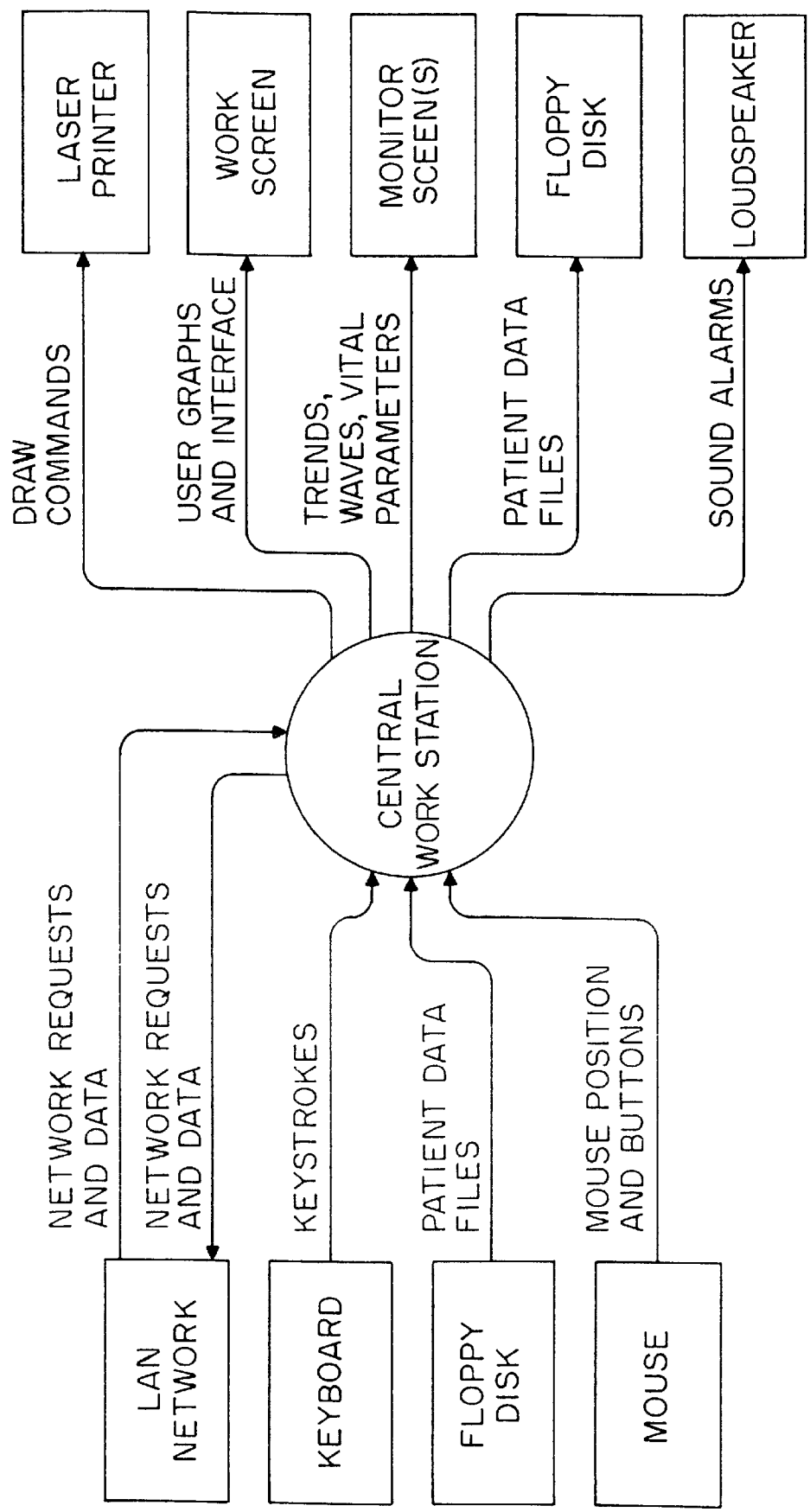
FIG. 8 is a block diagram graphically illustrating the connection of the central workstation to other components of an apparatus employing the invention.
Figure 13:
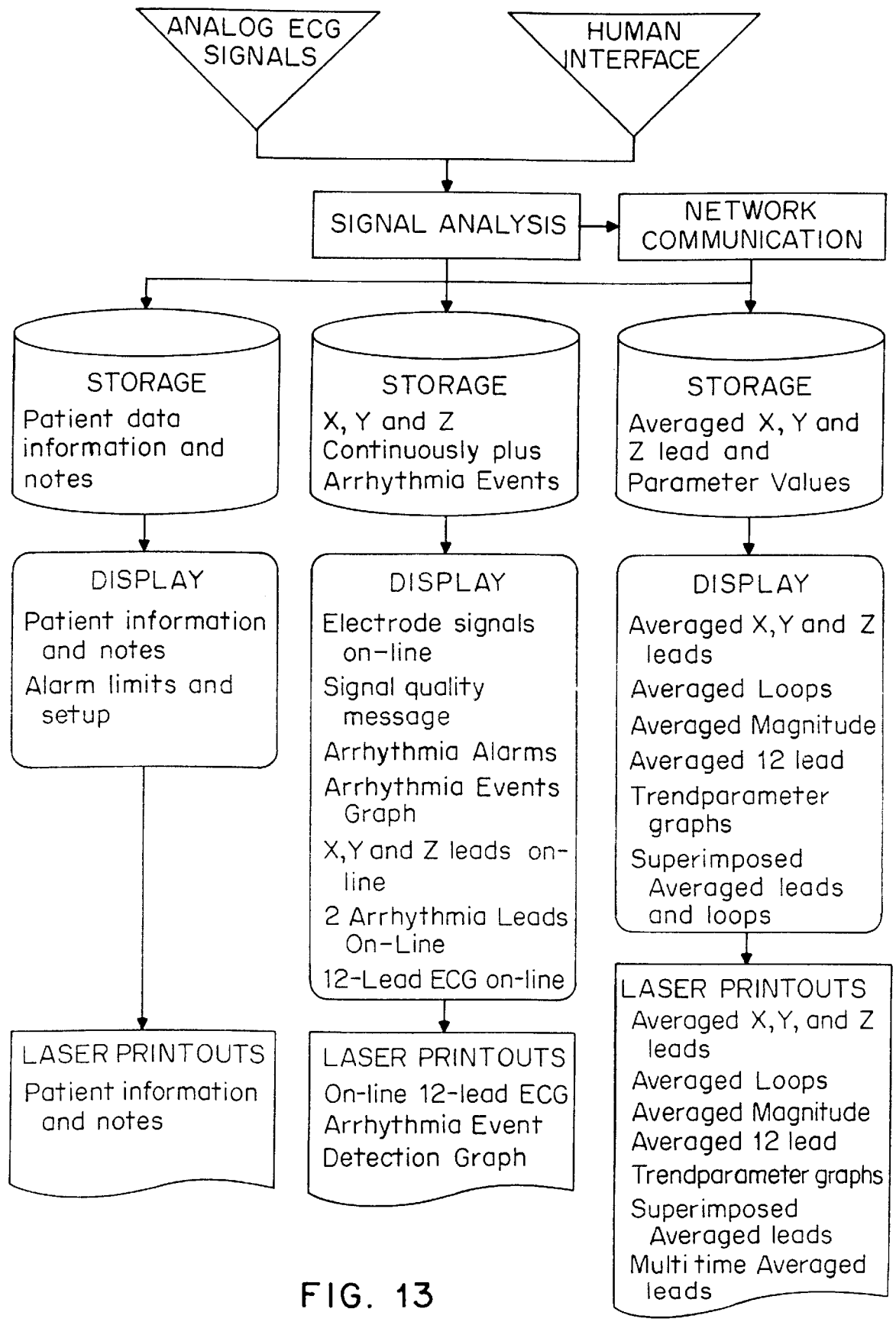
FIG. 13 shows the overall input/output possibilities in an apparatus employing the invention.

The central workstation is preferably a networking personal computer operating with specialized menu-driven applications software. An exemplary connection of the central workstation to other components is shown in FIG. 8 and an exemplary illustration of the functions which may be performed is shown in FIG. 13. The central workstation provides a straightforward and simple user interface operated through the selection of "keys" in a graphical display. Each key has an instructive text or symbol describing the function of the key. A mouse (or other pointing device) is used to point to and select a desired key. (In the examining functions, the mouse is also used to point out the ECGs to be enlarged, etc.) The surface of a key is normally grey. However, active keys are made yellow and void keys that cannot be accessed are dark grey.

Figures 9, 10:
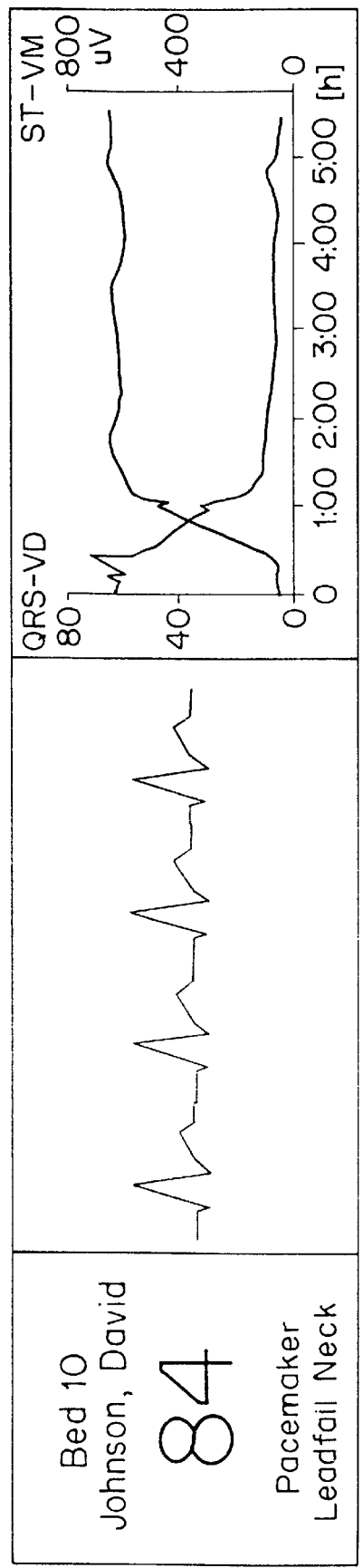
FIG. 9 is a diagram showing the top part of a graphical interface display which appears on the central workstation of a system employing the invention.
FIG. 10 is a diagram showing an example of the display format used for monitoring each patient on a central monitoring unit.
Figure 11:
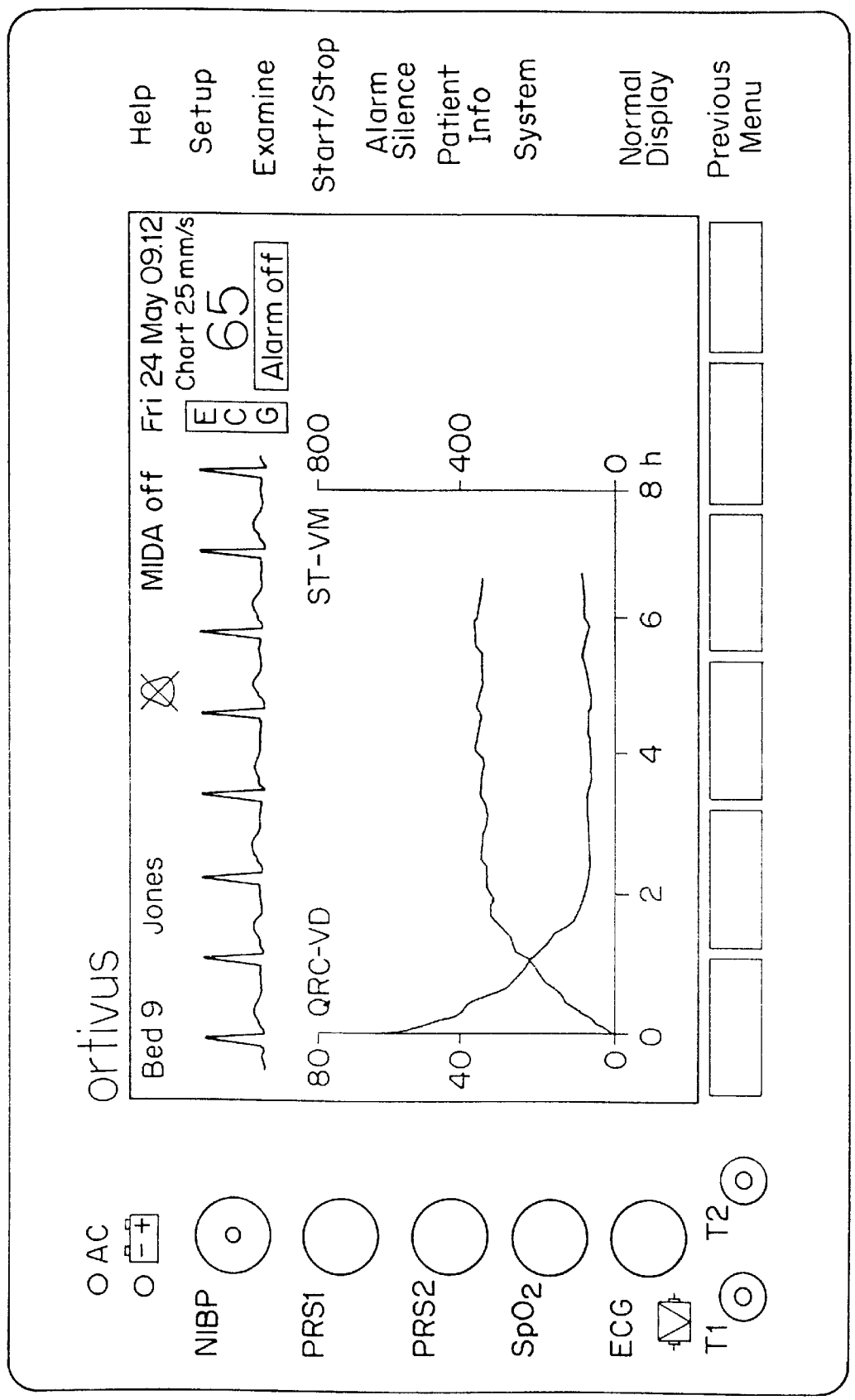
FIG. 11 shows the front face of a bedside monitor used in a first embodiment of a system employing the invention.

FIG. 9 shows an example of the initial menu displayed in an upper portion of the display in a preferred embodiment of the invention. There are two rows of keys. The keys in the top row are labeled with numbers corresponding to each one of a number of patients, System, Signal Status and Stored Patients. The lower row of keys preferably contains key commands for examining a patient file. For example, the keys may be labeled as Patient Info, Alarm, Report, Trend, ECG & VCG, Arrhythmia Events, ECG MIDA, ECG Review, All Leads and Setup. The keys are used to select and control all functions, both on the central monitors and on the workstation itself.

Signal status messages are displayed on the display of the workstation if no central monitor is in use. (Otherwise, signal status messages are always displayed on the central monitor.) A red patient key is used to indicate that something is wrong, that there is bad signal quality or problem with the analysis or other errors. If so, the reason may be seen in the Signal Status function. A crossed over key is used to indicate that the analysis has paused. The actual message for a specific patient is then displayed to the right of the patient name in the upper part of the workstation display.

CENTRAL MONITORING UNITS

All parameters available to the central workstation may be displayed as trend graphs on one or more central monitoring units 10. The central monitoring unit(s) 10 display the "live" situation of a plurality of patients simultaneously. The central monitoring units are preferably large (e.g., 17- or 21-inch), high-resolution computer monitors such as that shown in FIG. 7. Software display drivers in the workstation utilize high resolution graphics and the display is preferably at least 1024×768 pixels resolution. The monitors may continuously and simultaneously monitor ECG waveforms, vital parameters, alarms and vital ischemia trendings for each of a number of patients.

Arrhythmia alarms are presented in red letters on the displays and a 24-hour full disclosure arrhythmia review function offers complete control and documentation of all arrhythmias. The central monitoring unit(s) 10 also enable examination of derived 12-lead ECGs of every minute monitored. All other functions are displayed and controlled on workstation.

The information on the monitors is fixed in order to always present the current status of all patients. All interactive functions and examination of patient data which appears on the monitors is controlled from the workstation. The left half of the monitor screen presents conventional monitoring including heart rates and patient information, waveforms, arrhythmia alarms and optional vital signs while the right-hand side presents the ischemia trends. The graphs display the ischemic evolution of each monitored patient starting from a designated time, such as the patient's admission. The graphs are continuously updated to always include the most recent values. Up to six patients may be monitored on each display. When more than four patients are monitored, additional monitors may be used. The network 14 allows the selection of any two waveforms from each bedside patient monitor to be displayed on the central monitor. The waveform selected to be displayed on the central monitor need not be the same waveform selected for display on the corresponding bedside monitor 13. An example of a trend graph displayed on the central monitor for a single patient is shown in FIG. 10. The signal status and MIDA messages are identical to the ones displayed in the Signal Status overview of the display for the central workstation discussed later.

The content of the display of a respective patient on the central monitors (leads, filters, size and speed) is selected by central workstation 11 in the manner described below. The same information is always displayed at the same location in the display for improved functionality. The left side of the display contains bed number 101, patient name 102, heart rate 103, pacemaker information 104 and signal status message 105. The right side of the display contains trend graph(s) 106 and MIDA recording status message 107.

A patient is chosen for monitoring by clicking the number key corresponding to the patient in the top row of keys on the Workstation.

The Setup Menu key is selected to adjust the patient's display. If the Monitored ECG Lead key of the Setup Menu is selected, then a picture is displayed which contains the waveform for each of the patient leads along with a respective corresponding key, as well as keys for selecting the filtering, curve size and sweep speed of the displayed waveforms. If waveforms other than ECG leads, such as Spo2 and PA pressure, are monitored, then these appear in the display as well and are controlled in the same manner as the ECG leads. The primary waveform to be displayed on the central monitor is selected by clicking the corresponding key.

The setup menu in the first embodiment displays three filter keys which enable the displayed waveform to be filtered for improved visual impression. The first key, "None", displays the waveform unfiltered. The second key is labeled "0.05–100 Hz" and gently filters the curve from baseline variations below 0.05 Hz and noise above 100 Hz. The third key is labeled "0.5–40 Hz" and filters the displayed curve from baseline variations below 0.5 Hz and noise above 40 Hz. The setup menu in the preferred embodiment also displays three ECG size keys which set the size of the displayed waveform. When the "Auto" key is selected, the size of the displayed curve is continuously adopted to fill two thirds of the height available for the curve. The adoption is very slow so that if the original amplitude of the curve slowly decreases (maybe due to necrosis), the automatic adoption may result in an unaffected curve on the monitor. The "10 mm/mV" key sets the amplitude of the displayed curve to 10 mm/mV. The "20 mm/mV" key sets the amplitude of the displayed curve to 20 mm/mV.

All curves on the central monitor have the same speed. The speed may be set to 25 mm/sec or 50 mm/sec via selection of the appropriate key.

For all patients, a second monitoring curve (additional ECG, pulseoximetry or pressure) may also be selected for display in addition to the primary curve. This function is controlled by selection of a key marked "On/Off" which appears under the header "2nd wave" in the setup menu display. Selecting the On/Off key activates the second curve. A key marked "Wave 1" is selected to enable control of the upper curve (lead, filter, etc.). A key marked "Wave 2" is selected to enable control of the lower curve.

The Patient Info key allows inputting of the patient's name, ID, original symptoms and physician comments. The information is entered on respective lines using the keyboard in typewriter fashion and then pressing the enter key. The Patient Info menu also contains a Pacemaker key which is selected to indicate that the patient has a pacemaker.

The menu also has an Add note feature which permits the entering of notes and observations at the workstation at any time. When the Add note key is selected, a field is opened at the bottom of the display, the time is automatically displayed, and the Add note key is changed to a save note key. The text of the note is entered and edited using the keyboard.

The note is saved by clicking on the Save Note key. If the patient's waveforms are stored for subsequent analysis, the system stores all notes as well. They may be reviewed and printed on paper at any time.

The Patient Info menu is closed by selecting either a Save Patient Info key or a Cancel key. When a patient is discharged from the bedside monitor, the central workstation stores all recordings, including 24-hour full disclosure arrhythmia, by default until the storage capacity is needed for new recordings. When capacity is full, the oldest recordings will be erased automatically.

Once the patient has been entered into system as described aboved and the display for he central monitor has been formatted as described above, the system then commences on-line myocardial ischemia dynamic analysis and monitoring (MIDA) for treating patients with myocardial infarction, unstable angina or when monitoring patients during and post-PTCA.

Figure 4:
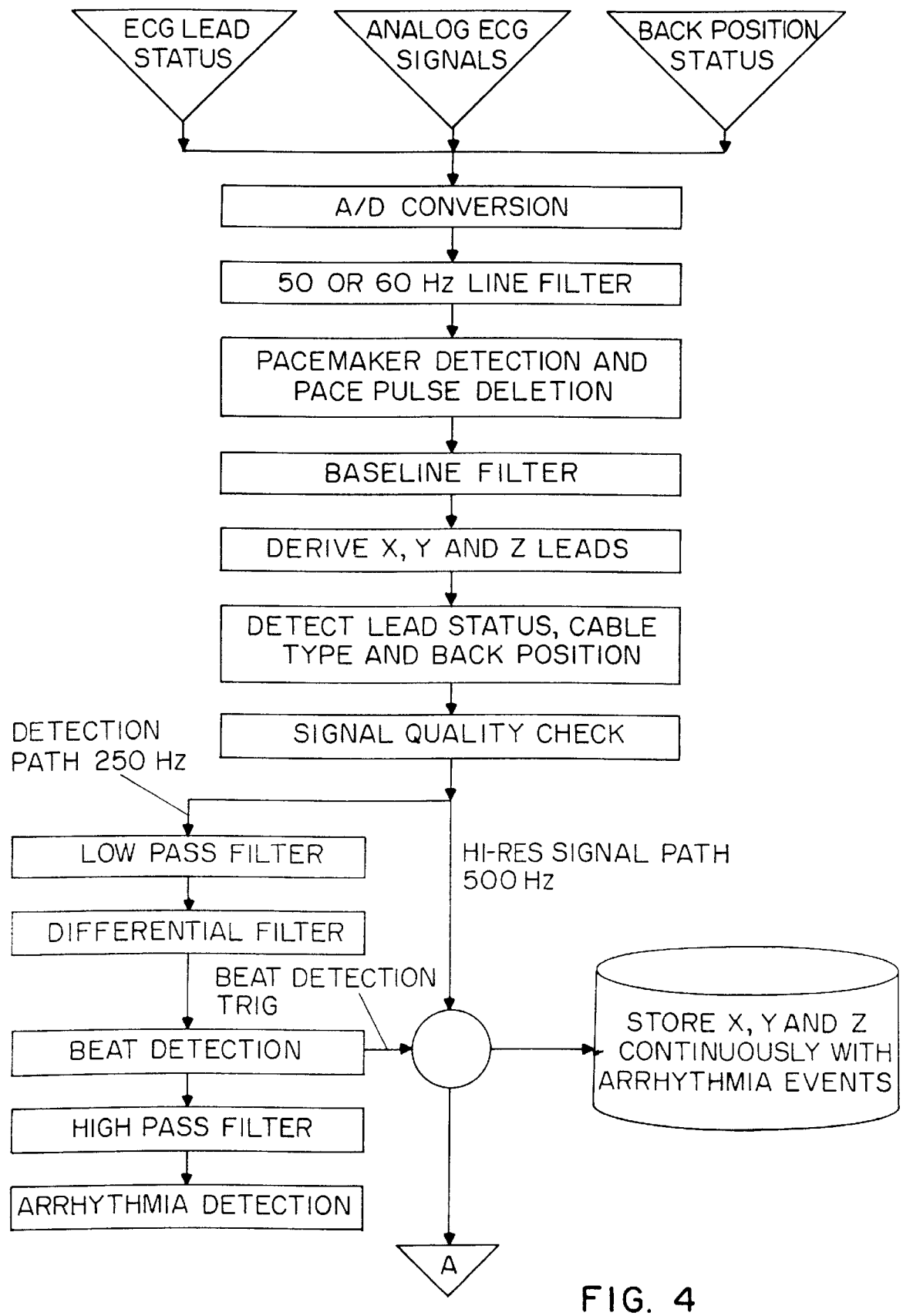
FIG. 4 is a flowchart depicting the manner in which three perpendicular leads (X, Y, and Z) are produced in a preferred embodiment of the invention.

Based on the electrical signals from eight ordinary surface ECG electrodes placed according to Frank, three perpendicular leads (X, Y, and Z) are produced in the manner shown in FIG. 4. The method used in the system permits ischemia monitoring based on Frank leads, analyzing the X, Y, and Z signals to achieve unique parameters, such as ST-VM, QRS-VD and STC-VM, which are displayed in a trend chart.

Figure 5:
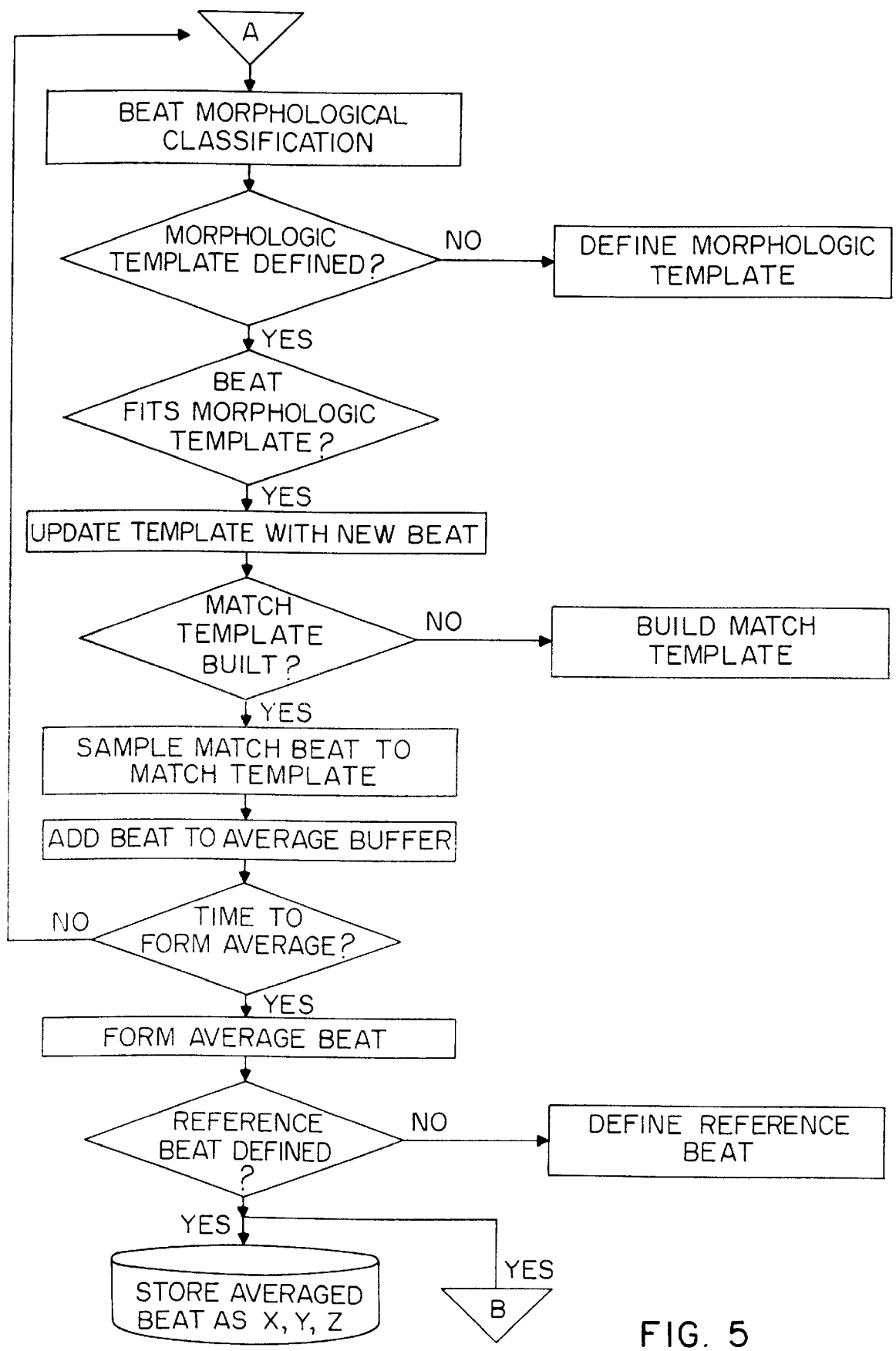
FIG. 5 is a flowchart showing the initial steps in the analysis and monitoring used in the preferred embodiment of the invention.

When monitoring starts in the manner shown in FIG. 5, beats undergo a morphological classification and a morphological template is defined. If a beat fits the morphological template, a match template is built, such by selecting a normal ECG beat to serve as the template. Beats are compared to the match template to determine which beats are "normal" beats that should be included in the analysis and which beats should be excluded from the MIDA analysis. During the remainder of the analysis, the three leads X, Y and Z are continuously scanned for "normal" beats. When a normal beat is found, it is matched and included in an average of the acquired normal beats formed at even time intervals, preferably every minute provided that the quality of the signal is sufficient. The ECG from the first average beat is referred to as the Reference Complex and used as a reference to which the ECGs from all subsequent beats are compared to see the relative change over time.

Figure 6:
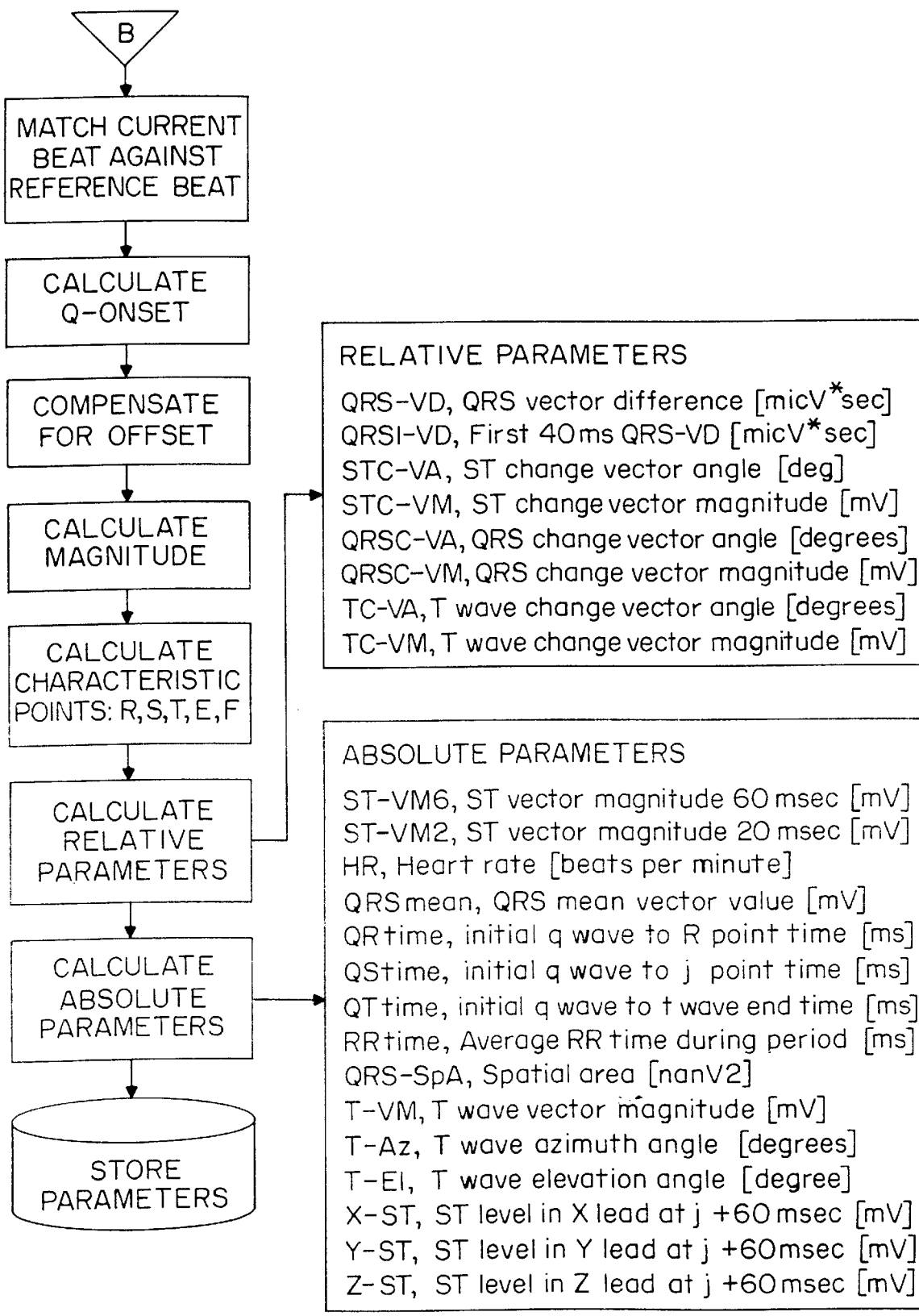
FIG. 6 is a flowchart depicting the manner in which the averaged beat, represented by the averaged X, Y and Z leads, undergoes advanced calculations to determine parameters describing the condition of the ECG.

At even time intervals between a range of 10 seconds and 4 minutes, the averaged beat, represented by the averaged X, Y and Z leads, undergoes advanced calculations as shown in FIG. 6 to determine up to thirty different parameters describing the condition of the ECG. The parameters are stored in addition to the 5 averaged ECG itself.

There are two kinds of parameters: absolute and relative. Absolute parameters are calculated from the actual ECG complex itself. Relative parameters are calculated from the difference between the current ECG complex and the initial reference complex to reflect serial changes over time.

The following are examples of absolute parameters: QRSmax, QRSmean, ST-VM, ST-VM2, X-ST, Y-ST, Z-ST, QRS-SPA, HR, QRtime, QStime, QTtime, RRtime, T-VM, T-Az, T-El, X-ST, Y-ST, Z-ST and Abnorm.

QRSmax (mV) is the maximum magnitude within the QRS-complex.

QRSmean (mV) is the mean magnitude of the ECG-vector during the time ranging from QRS onset up to QRS end of the initial QRS-complex.

Figure 2:
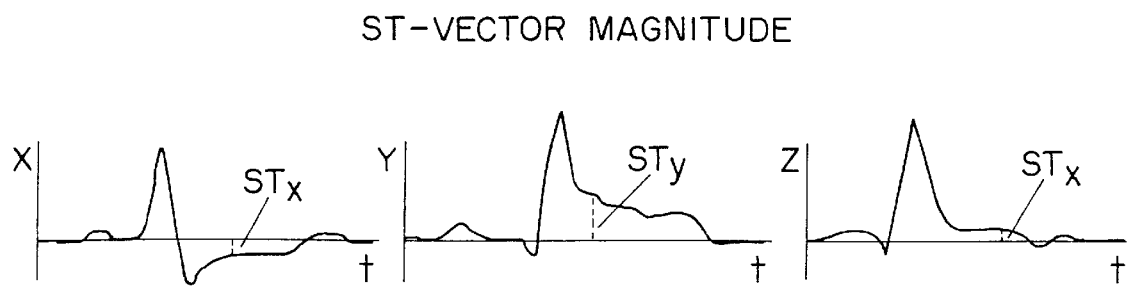
FIG. 2 is a graphical representation illustrating the ST-VM parameter.

The ST vector magnitude (ST-VM) measures the total offset of the ST-segment and is commonly accepted as a measure of ischemia in the myocardium during ischemia. It is measured in every averaged beat, 60 milliseconds after the J point (the end of the QRS complex). The values from the X, Y and Z leads are fed into the formula:

$$ST\text{-}VM = \sqrt{S_x^2 + ST_y^2 + ST_z^2}$$

and the resulting ST-VM value is plotted in the trend graph. The way the formula is constructed, an ST elevation in one lead does not neutralize an ST depression in another lead. Both elevations and depressions are detected simultaneously. See FIG. 2. Since the ST segment is measured in both the X, Y and Z leads, it provides one ST measure that covers the entire heart.

ST-VM2 (mV) is the ST vector magnitude 20 ms after the J point.

X-ST (mV) is the ST level in the X lead 60 ms after the J point.

Y-ST (mV) is the ST level in the Y lead 60 ms after the J point.

Z-ST (mV) is the ST level in the Z lead 60 ms after the J point.

QRS-SPA (nanV$^2$) is the area in the space drawn by the ECG-vector from the point of the initial QRS onset to QRS end. HR (beats per minute) is the mean value of the heart rate during the MIDA interval.

QRtime (ms) is the time between QRS onset and the maximum magnitude of the current complex.

QStime (ms) is the time between QRS onset and QRS end of the current complex.

QTtime (ms) is the time between QRS onset and the maximum magnitude within the T wave of the current complex.

RRtime (ms) is the mean value of the RR intervals during the averaging period.

The T vector magnitude (T-VM) measures the maximum magnitude within the T-wave of the current complex in mV. The ECG-vector in this point is called the T-vector.

T-Az is the angle of the T-vector in the transversal plane, 0 to 180 degrees from sinister to dexter, and positive if anterior and negative if posterior.

T-El is the angle of the T-vector from the vertical axes, 0 to 180 degrees from dist to cranium.

Abnorm is the number of abnormal beats during the averaging period. All beats that are not classified into the reference class are labelled abnormal.

Figure 3:
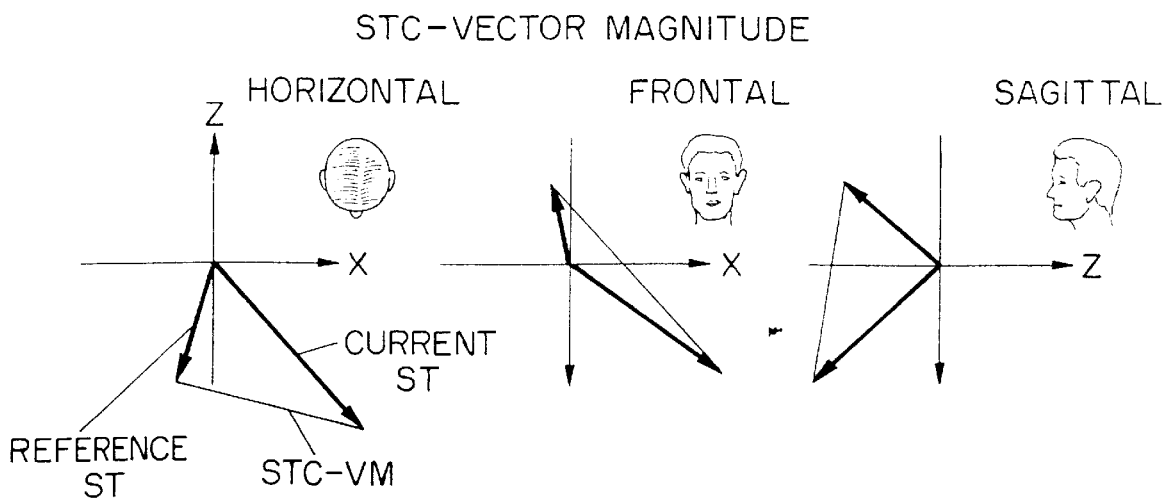
FIG. 3 is a graphical representation illustrating the STC-VM parameter.

The change of the ST magnitude compared to when monitoring was 15 started (STC-VM) is also calculated as shown in FIG. 3. The ST differences are fed into the formula:

$$STC\text{-}VM = \sqrt{STC_x^2 + STC_y^2 + STC_z^2}$$

Figure 1:
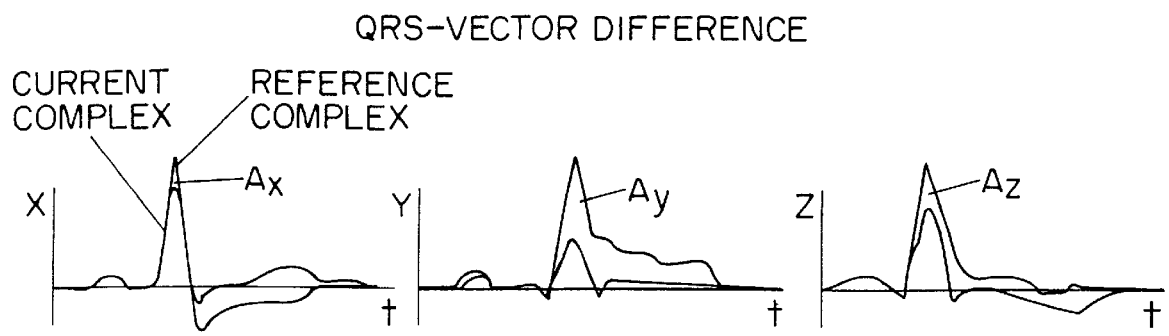
FIG. 1 is a graphical representation illustrating the QRS-VD parameter.

The following are examples of relative parameters: QRS-VD, QRSI-VD, QRSA-VA, QRSC-VM, STC-VA, STC-VM, TC-VA and TC-VM. The QRS vector difference (QRS-VD) measures changes in the QRS complex compared to the initial ECG and reflects the change in morphology of the QRS complex caused by, e.g. necrosis and temporary ischemia compared to when monitoring was started. The complex is compared to the initial QRS complex and the arial difference ($A_x$ in FIG. 1) is calculated in the X, Y and Z leads.

The values are fed to the formula:

$$QRS\text{-}VD = \sqrt{A_x^2 + A_y^2 + A_z^2}$$

and the resulting QRS-VD is plotted in the trend graph.

QRSI-VD (mVs) is the initial QRS vector difference which is the same as for QRS-VD except that the areas $A_x$, $A_y$ and $A_z$ range from QRS onset of the initial QRS complex and 40 ms forward.

QRSC-VA is the QRS vector angle change and represents the change in the angle between the current and initial QRS vectors.

QRSC-VM (mV) is the QRS vector magnitude change and represents the distance between the initial and current QRS vectors.

STC-VA is the ST vector angle change and represents the change in the angle between the initial and current ST vectors.

STC-VM (mV) is the ST vector magnitude change and represents the distance between the initial and current ST vectors.

TC-VA is the T vector angle change and represents the change in the angle between the initial T-vector and the current T-vector.

TC-VM (mV) is the T vector magnitude change and represents the distance between the initial and current T-vectors.

Selected ones of the relative and absolute parameters describing the course of the ischemia may be chosen for display and plotted in a trend graph. The three most common are the QRS-VD (morphological changes) and ST-VM (st-measurements) and STC-VM (st changes).

Figure 14:
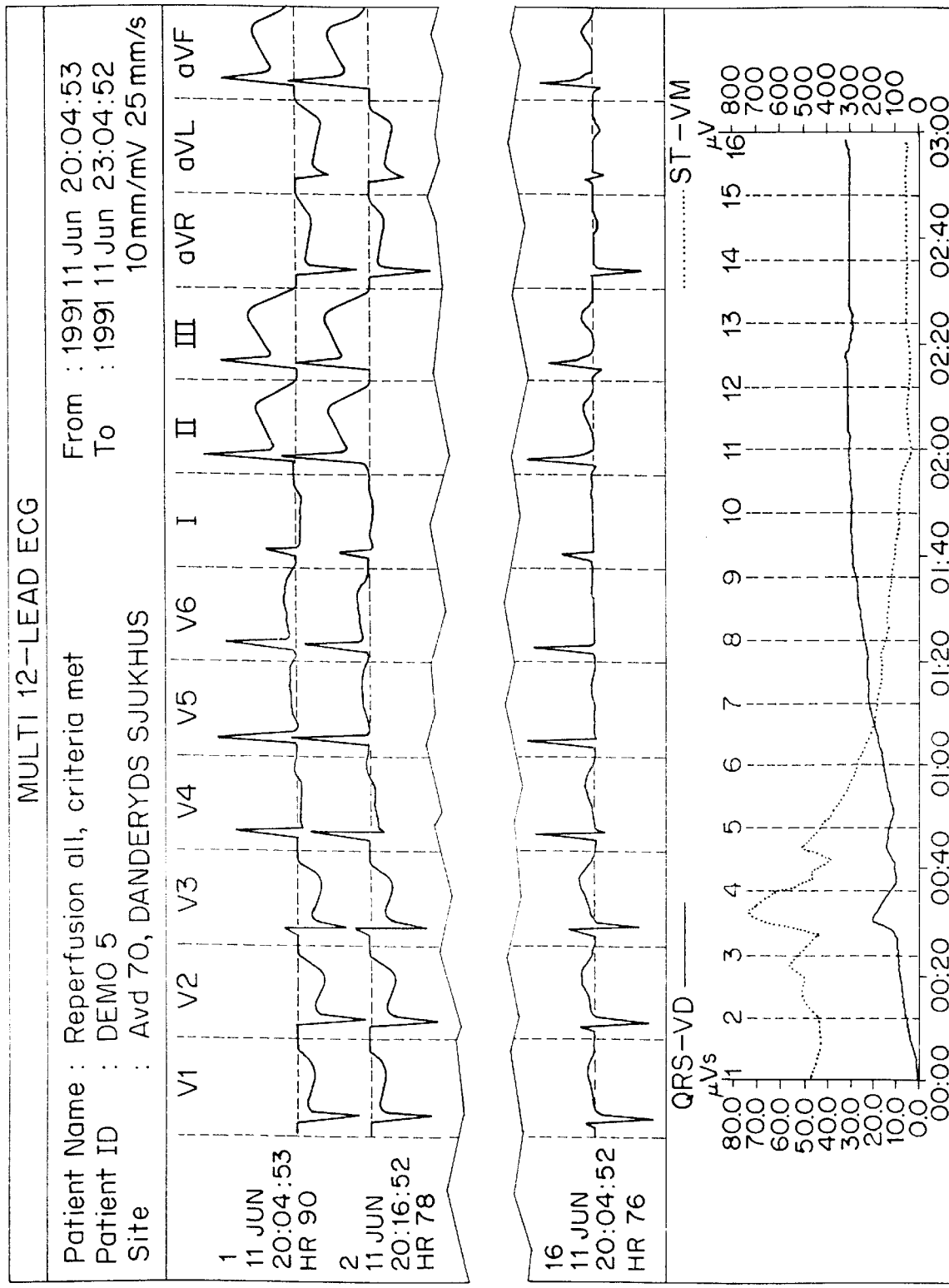
FIG. 14 shows an example of a single page printout, having a plurality of ECG signals printed under each other, produced by the invention.

The averaged ECG that is stored at the end of each time interval contains the values for each of the X, Y, and Z leads. Since the X, Y, and Z contains all information of the ECG, it may also be used to calculate a full 12-lead ECG in real time using a known algorithm. This way, the preferred embodiment may also continuously display a calculated averaged 12-lead ECG for every minute during the entire monitoring period of up to 48 hours in the format of a 12-lead ECG on central workstation 11. Based on the continuously stored X, Y and Z leads, a continuous calculated 12 lead ECG could also be displayed next to a chart with the occurrence of arrhythmias over a selectable range of hours marked as colored bars. The preferred embodiment may also produce a single page printout with a plurality of 12-lead ECG signals printed under each other. See, for example, FIG. 14. The MIDA trends for each patient may be examined in detail one at a time on the workstation display. The trends of all patients may be monitored continuously on the central monitor using the format shown in FIG. 10.

Depending on the amount of memory provided, the MIDA recording may last, for example, only approximately 48 hours at one-minute intervals. After that, the memory is full and the recording is automatically stopped. Below is an exemplary chart comparing MIDA time intervals to maximum length of the recording.

| MIDA Time Interval | Maximum Length of Recording |
| --- | --- |
| 10 seconds | 8 hours |
| 15 seconds | 12 hours |
| 30 seconds | 24 hours |
| 1 minute | 48 hours (two days) |
| 2 minutes | 96 hours (four days) |
| 4 minutes | 192 hours (eight days) |

The arrhythmia full disclosure works differently, always keeping the most recent 24 hours in memory.

The setup menu contains a MIDA Relearn key to control the MIDA method. When the MIDA Relearn key is selected, the workstation display shows the latest ECG signals acquired with beat labels (beat labels are updated approximately 30 seconds). Every detected QRS complex is labelled with an "M" if it is recognized as a MIDA type of beat (matches the MIDA template). The present MIDA Reference Complex is displayed to the left of the 20 waveforms as scaler X, Y and Z leads. This is the actual, initial, averaged beat to which all subsequent beats will be compared when calculating the relative trend parameters.

The system provides a Restart MIDA key in the MIDA setup display for beginning the process over again. If the Restart MIDA key is selected, a warning message is displayed with options to cancel (No/Cancel) or proceed (Yes). Then a message "Selecting MIDA template, please wait for 20 seconds" is displayed with an option to cancel.

If the process is not cancelled, a suggested new template is displayed in a square for consideration by the user along with three keys for selection. If the Yes key is selected, the entire previous MIDA recording is erased, the suggested template is accepted and the method is restarted. The display is reset, but with no MIDA Reference Complex displayed, since no new Reference Complex has yet been formed. If the No key is selected, the template selection procedure is restarted and a message asking the user to wait for 20 seconds is displayed.

The MIDA system also includes a "MIDA Relearn" feature, the steps of which are identical to the Restart MIDA command described above except that the previously recorded and stored data is not erased.

This feature is appropriate when the MIDA analysis is no longer capable of tracking the ECG. MIDA relearn will find a new template for including ECG complexes in the analysis. (ECG changes always refer to the initial, reference ECG.)

The system also permits the user to review the MIDA Signal Status 107 included in the display, shown in FIG. 10, for each patient. The signal status for all patients is displayed in a Signal Status table when the Signal Status key in FIG. 9 is selected. Below is a list of different possible MIDA signal status messages in order of priority. The line with message of highest priority is indicated with a red background.

1) No MIDA Recording possible with current patient cable. An 8-lead cable is needed for the MIDA recording. If a 5-lead cable is in use, this message is shown.
2) MIDA Recording Ended. The MIDA Recording may last for a maximum of 48 hours with one-minute intervals. When memory is full, the recording is automatically stopped and this message is shown.
3) No MIDA Recording due to Spikes on signal. A signal spike is a very short disturbance of considerable signal strength. The orgin of the disturbance may be pacemaker spikes, bad lead wires or electromagnetic radiation from other equipment. The system will automatically turn the spike filter off if the patient has got a pacemaker, as indicated in the Patient Info function.
4) No MIDA Recording due to Noisy Signal. Noise may be caused by many reasons. Bad patient electrode connection may be one reason. Line disturbances from other equipment close to the patient cable may be another.
5) No MIDA Recording due to Baseline Drift. If the baseline drift is too big, this may distort the ECG. To prevent this, the MIDA Recording is halted. (Baseline drift is a variation in the offset voltage)

6) No MIDA Recording due to lead fail. One of the ECG leads is not working properly.

7) No MIDA Recording due to no reference type of beats. This message is active if the minimum number of reference type of beats was not received during the previous MIDA interval.

Figure 15:
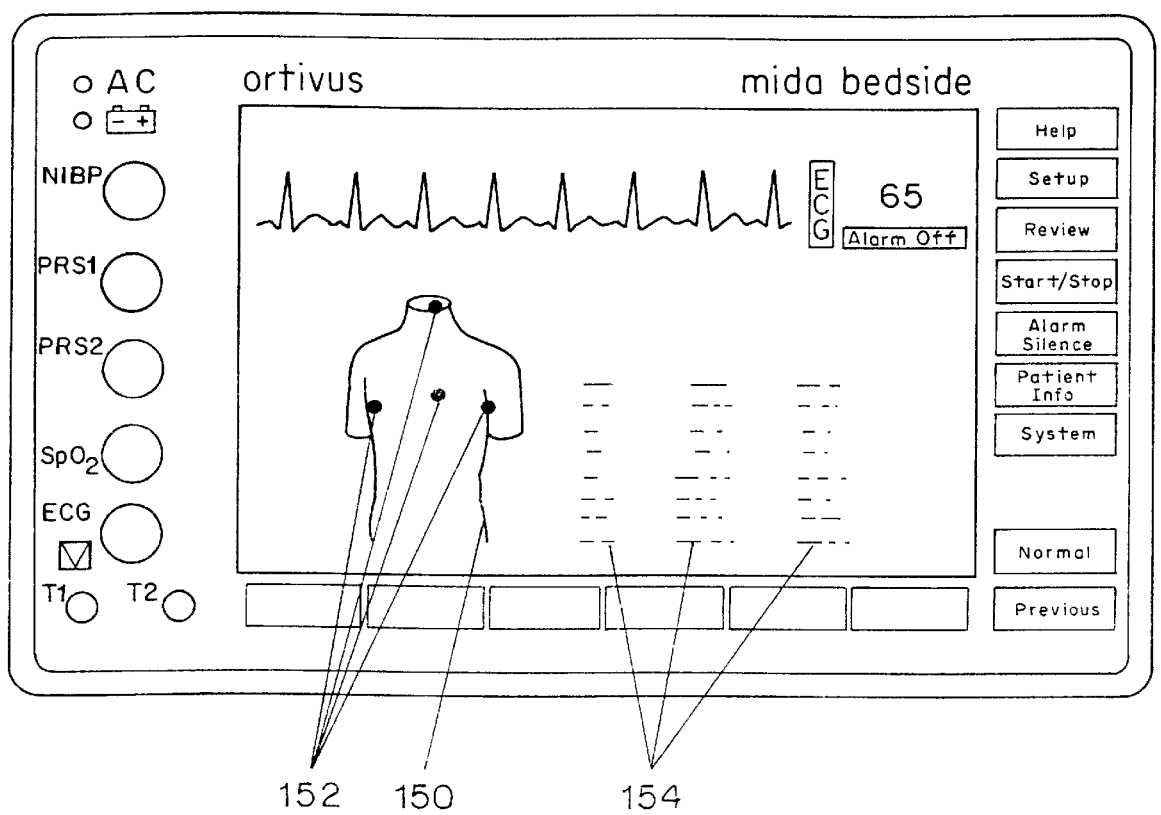
FIG. 15 shows a the display of a patient's torso on a display device along with electrode status indicator lights and annunciator means.

In another embodiment of the invention shown in FIG. 15, a graphical depiction of at least part of the patient 150 is provided and status signal lights 152 corresponding to each electrode connected to the patient are disposed on the graphical depiction 150. Further, status annunciator means 154 corresponding to each electrode, which may provide alphanumeric output, may be provided for indicating the status of each electrode. The status of each electrode (whether a MIDA test is being done or not) may be one of conditions 3, 4, and 5 discussed above, for example. In addition, the status annunciator means may indicate that an electrode has failed, is not properly connected to the body, or in fact has even fallen off, which conditions are manifested as a high electrode impedance. Further, the impedance itself may be displayed by the status annunciator means. The status signal lights may blink to call attention to the status annunciator means and to pinpoint to which electrode(s) the information conveyed by the status annunciator means are directed. The display may be any suitable means, such as a CRT (color or monochrome), active LCD (TFT), passive LCD (SDN), plasma, electroluminescent (EL), or ferro LCD, for example. The display may also be produced by a projector.

The system may also utilize a back position sensor. Since the heart is relatively mobile in the chest, it is only natural that it changes position within the chest when the patient changes position in the bed, e.g. from lying on the back to lying on the side. Since the electrodes record the electrical activity on the surface of the chest, the movement results in a change in the ECG. The influence of this change affects each of the MIDA parameters differently. Since ST-VM measures the strength of the ST deviation, regardless of direction, it is less sensitive than other "ordinary" ST measurements. The parameter QRS-VD is, however, very sensitive to these changes. A back position sensor makes it possible to tell if a change in the trend was caused by change of body position or not.

The Back Position Sensor connects to the junction block of the 8-lead ECG cable. The information from the back position sensor is recorded and displayed on a separate line below the trend graph. This line may have three colors indicating the following states:

| Color | State |
|-------|-------|
| Green | On Back |
| Yellow | Not On Back |
| Grey | No Trend available |

The MIDA trend may be displayed on the central monitor as described previously. The Trend key also arranges for the picture to be displayed on the display of the workstation for review.

Keys appear to the left allowing the user to select what trend will be displayed. These keys may be labelled MIDA and HR/PVC. Up to four different trend curves may be displayed in the trend graph. To be able to tell the curves apart, they are displayed in different colors. The name of each trend curve is 5 also written over the graph in the same color as the curve itself.

The system provides a cursor, controlled by the mouse, in order to, for example, mark points of special interest. (If points of special interest are marked in the trend curve, they may be of assistance when examining the corresponding 12-lead ECGS.) By pointing and clicking in the trend, the cursor is moved to the desired time. Alternatively, the cursor may be moved step by step by pressing the right and left arrows under Cursor labels on the bottom of the display of the trend graph. The system displays time of the trend graph corresponding to the position of the cursor on the top of the graph, both as time of day and time since admission. The system also displays the exact values of the parameters to the left and to the right of the time.

Points are marked by placing the trend cursor at the desired time and selecting the check key which is displayed between the arrows under the Mark label to the right under the graph. When the trend cursor is placed on a marked time, the system turns the check key to yellow.

The user can jump directly between separately marked times by selecting the right and left arrows under the Mark label. The system unmarks a time whenever the user presses the check key again.

The system also permits the user to change the parameters in the trend graph. (Users normally select the QRS-VD and ST-VM6 parameters for display in the trend graph. The MIDA analysis includes thirty parameters that are continuously calculated and stored.) The MIDA trend display contains keys under the Trend parameter label which select the axis to be affected (Le1=Left one, Le2=Left two, etc.). A table of different parameters will then be displayed in response to the selection of an axis. The user then selects the key of the desired new parameter to be trended. A Return key is selected to return to the graph.

The system further permits adjustment of the timescale of the trends to include the most interesting parts of the trends. Zoom keys are displayed, which, when selected, make it possible to enlarge certain parts of the trend curves. The system is set up so that "zooming" is centered around the cursor, which can be placed in the middle of the interesting part of the trend curves by pointing and clicking with the mouse. Every time the left "-" zoom button is pressed, the curves around the cursor are expanded. The right "-" zoom button has the reverse effect; it goes back and shows bigger portions of the curves.

The system also provides a Scale key, which when selected displays additional keys which enables the user to adjust the size of the displayed graph. The height of the trend graph(s) may be increased or decreased by selecting arrows under the Max label to the left and to the right of the graph. The baseline offset may be adjusted by selecting the arrows under the Offset label.

After the scales have been changed, they may be reset to default at any time by pressing the Normal key.

Again, a Return key must be selected to return to the graph. The system further allows the time to be changed with a key displayed on the bottom right hand side. Clock time is the time of day (8:30 means eight thirty in the morning) while Relative time is time since admission (8:30 means that the patient has been monitored for eight and a half hours).

It is also a particular advantage of the system employing the method that a number of settings controlling the MIDA analysis may be adjusted to customize the analysis. The MIDA setup is available through the MIDA Setup key.

The different settings are described below, one by one. Each group of settings may be reset to default values individually by pressing the Normal key next to each group.

The MIDA interval is the time interval within which the MIDA analysis will produce new values. During each interval, all acquired ECGs of sufficient signal quality that match the initial reference ECG will be averaged to form an ECG with improved signal quality. At the end of the interval, the averaged ECG is used when calculating the MIDA parameters. The averaged ECG and the 5 parameters values of every such interval is stored in the Acquisition Module for approximately 3000 intervals.

Short intervals (less than 1 minute) have the advantages of fast response to rapid ECG changes, but they also have more noise and result in a shorter total recording time. Long intervals (more than 1 minute) have less noise and result in a longer recording time but they also respond slowly to rapid ECG changes. Generally, one minute intervals are recommended for CCU monitoring (infarction, unstable angina, etc.) and 15 second intervals are recommended for PTCA use. The default setting is preferably 1 minute.

To form an averaged ECG at the end of the intervals previously described, a minimum number of beats must have been included in the average. Too low a limit may result in poor signal quality. Too high a limit may result in difficulties reaching the limit with no calculated parameter values as a result. Naturally, the minimum number of beats required is dependent on the interval length.
Recommended settings:

| MIDA interval | Minimum number of beats |
| --- | --- |
| 10 seconds | 1 beat |
| 15 seconds | 1 beat |
| 30 seconds | 2 beats |
| 1 minute | 2 beats (factory setting) |
| 2 minutes | 10 beats |
| 4 minutes | 10 beats |

If the signal quality of the acquired ECG is too poor, the ECG will not be used for MIDA analysis. This is to avoid false results—artifacts. Each ECG signal has to pass the following tests to be included in the MIDA analysis.

A signal spike is a very short disturbance of considerable signal strength. The origin of the disturbance may be electromagnetic radiation from other equipment, bad lead wires or pacemakers. The spike test may be turned on or off. When spikes are detected, the MIDA analysis is halted unless the patient has a pacemaker.

Noise may be caused by many reasons. Bad patient electrode connection may be one reason. Line disturbances from other equipment close to the patient cable may be another. The noise threshold may be set to 5, 10, 20, 50 or 100 micV or may be turned off. When excessive noise is detected, the MIDA analysis is halted. The default setting is 50 $\mu$V.

If the baseline variation is too big, this may distort the ECG. The baseline threshold may be set to 25, 50, 100, 200 or 400 micV/second or be turned off. When baseline variation is detected, the MIDA analysis is halted. The preferred default setting is 100 micV/sec.

The default settings may be selected by the user in a table of default settings which is opened by selecting the System key and entering an access code. The table includes a Save key and a Cancel key which, when selected, respectively set the default settings or close the menu with no alterations to the default settings.

THIRD EMBODIMENT

A third embodiment of the invention may be used as a complement to a conventional monitoring system for enhanced monitoring and documentation of the ECG in terms of ischemia, infarction and arrhythmia.

This embodiment also has the advantages of ischemia monitoring with parameters reflecting the ECG changes in clear trend graphs, averaged 12-lead ECG acquisition, storage and display, arrhythmia detection, 24-hour full disclosure arrhythmia of all monitored patients, and 24-hour continuous 12-lead ECG stored for all monitored patients.

However, this embodiment does not contain a monitoring system with waveforms and arrhythmia alarms. Rather, it is a system for only monitoring ischemia and the course of various heart diseases. Waveforms and alarms are controlled and monitored using the conventional monitoring system.

It consists of the elements shown in FIG. 7, except that instead of a bedside monitor, it has an Acquisition Module for each patient, connected via Ethernet to a central Server. The server displays and stores data from all connected Acquisition Modules. It is a supplement to a conventional monitoring system adding the functionality described with respect to the first embodiment.

The Acquisition Module works in parallel with the patient monitor of the conventional monitoring system. The ECG signal from the patient is fed into both the Acquisition Module as well as the patient monitor. The parallel connection is achieved with an adapter cable between the acquisition module and the patient monitor.

The Acquisition Module acquires the signal, converts it from analog to digital and performs ischemia and arrhythmia analysis. The Acquisition Module communicates with the central Server via an Ethernet connection on the back. It also includes a serial port for connection to other devices, such as the Hewlett Packard VueLink interface module.

FIG. 12 shows a face of an Acquisition Module. Element 121 is an ECG input for use with either 8-lead or 5-lead patient cables. Element 122 is a Signal out for connection to the ECG input of the conventional monitor. Element 123 is a graphic depiction of the patient, which in this case includes only the torso. More or less parts of the patient may be included in the graphic depiction of the patient, for example, the limbs. A number LEDs or other light producing means are placed behind the graphic depiction of the patient, each at positions corresponding to the electrodes on the patient's body. Each electrode may be indicated individually with a twinkling yellow light if the signal quality is poor or with a steady yellow light if the lead fails. When the signal quality is all right, all electrode indicators are off. Alternatively, the electrodes may blink at different rates or display different colors depending upon the conditions of the electrodes discussed with reference to the second embodiment. The graphic depiction of the patient may be silk screened, wet painted, powder coated, multi-color molded plastic, or overlay film, for example. Element 124 is a MIDA status indicator with a green and yellow indicator. The green indicator is on when MIDA analysis is running. If the MIDA analysis is not running for anyone of various reasons, the yellow indicator is on. Element 125 is a back position indicator. A back position sensor is a position sensitive device that may be used to record if the patient is lying on his back or not. This information may be useful when examining the most sensitive parameters such as QRS-VD of the MIDA analysis. When such a sensor is used, the back position indicator is green only when the patient is lying on his back. Element 126 is an event Mark key. When this key is pressed, an event mark is recorded by the system. Element 127 is a Pause key. The recording may be paused and resumed with this key. When paused, recording and analysis are temporarily halted. This is indicated with a yellow light behind the pause symbol. Element 128 is a Discharge Patient key. When this key is pressed, the current recording is terminated and the MIDA module is ready to start a new. Element 129 is a Main Power operation indicator. A green light indicates that the module is on, running on main power. Element 130 is a Battery Power operations indicator. A yellow light indicates (a warning) that the module is on, running on the internal battery for very limited time. Element 120 is an On/Off Switch. The module is turned on by pressing the switch. The module is turned off by pressing the switch again.

The patient input of the MIDA Acquisition Module is of Type CF, it is defibrillation proof (it may remain connected to the patient during defibrillation), and the patient connector on the front is marked with the appropriate heart symbol.

The patient input of the MIDA Acquisition Module is designed to limit the current through the patient to a few microAmperes and to comply with the requirements for low leakage currents when connected to a conventional Monitoring System. If other equipment than the MIDA Acquisition Module is connected to the patient, it should be interconnected with an equipotential grounding cable. On the back of the MIDA Acquisition Module there is an equipotential grounding terminal for this purpose. The following connections are provided on the rear (not shown) of the MIDA Acquisition Module:

AC in—to be connected to a grounded electrical AC source of 100–240 V+−10% , 50–60 Hz.

Equipotential grounding terminal—used to obtain the same electrical earth reference when additional electrical equipment is used together with the MIDA Acquisition Module.

Ethernet—for connection to the Ethernet network.

RS-232 Serial communication—for connection to other devices, such as a Hewlett Packard VueLink module.

The Acquisition Module is equipped with an internal battery that is switched in as soon as the AC power is insufficient. The internal battery provides full operation for at least five minutes, when fully charged. When the MIDA Acquisition Module operates on the internal battery, a yellow LED is lit in the lower right corner of the front, under the battery symbol. The internal battery is recharged as soon as the AC power is back and the Module is on. Line power operation is indicated by a green LED in the lower right corner, under the AC symbol.

Workstation 11 also contains a 17"color monitor on which curves and data from one patient at one time may be brought up for examination. The workstation also contains a graphical interface with a mouse, which may be used to control the operation of up to two of the central monitoring units. However, the central monitors are not disturbed at all when the monitoring of one specific patient is controlled or examined at the workstation. All information presented on the workstation at any time may be printed on the laser printer.

A row of keys on the top of the workstation monitor allows 5 selection and direct control of the monitoring of each patient. The keys are marked with an identification tag for each bed (normally 1, 2, 3 and so on). When a patient has been selected, the operator may control admission/ discharge, alarm settings, waveforms monitored, and much more in a straightforward and easy manner using the graphical interface. A monitoring session may also be examined in detail in terms of ischemia, 12-lead ECGs and full disclosure arrhythmias.

When the ischemia trends are examined on the workstation, any one of 30 different calculated parameters may be examined over time. Interesting events may then be expanded on the screen and exact values corresponding to the events will be shown. Short events can be expanded to display a couple of minutes on the display even if the entire trend covers several days of monitoring.

The system in the preferred embodiment of the invention reduces the need for additional 12-lead ECGS. Minute-by-minute, derived 12-lead ECGs are automatically acquired and stored in the system. Several 12-lead ECGs may be superimposed from different times in order to plot gradual changes. By pointing out interesting ischemic events in the ischemia graphs, the corresponding 12-lead ECGs may be displayed, superimposed or printed on the laser printer, if desired. Thus the morphologic nature of the ischemic changes may be examined in real time, i.e., during thrombolytic therapy or unstable angina.

Workstation 11 also contains a complete 24-hour full disclosure arrhythmia review function. The arrhythmia graph is presented on the lower half of the workstation display, with the arrhythmias plotted as colored dots or lines depending on the duration of the arrhythmias. The corresponding ECG is displayed on the upper half of the display. Every single heartbeat during the previous 24 hours can be displayed for each monitored patient by pointing out either the arrhythmia of interest or the desired time of day.

The system also contains a data storage unit for storing all data from the monitoring session for future examination. A stored recording may be examined on the workstation in exactly the same way as currently monitored patients.

The preferred embodiment of the invention described above uses a complete networking system for a number of patients to perform the following analysis and monitoring. However, this method of analysis and monitoring may be technically implemented using different hardware, system architecture or a special program code in a different program coding. The method may, for example, be used in a stand-alone system for a single patient.

The method may also be used in an ambulatory application. In such an application, ECG signals are recorded over a long period of time by a recording device worn or carried by the patient. The recorded signals are later retrieved for printout and analysis. The signals may then be analyzed according to the method described here below.

In a telemetry application, the patient carries a small transmitter which transmits the ECG signals to a receiver where the signals are displayed in real time. The ECG signals received by the telemetry system are then analyzed according to the following method.

Figure 16:
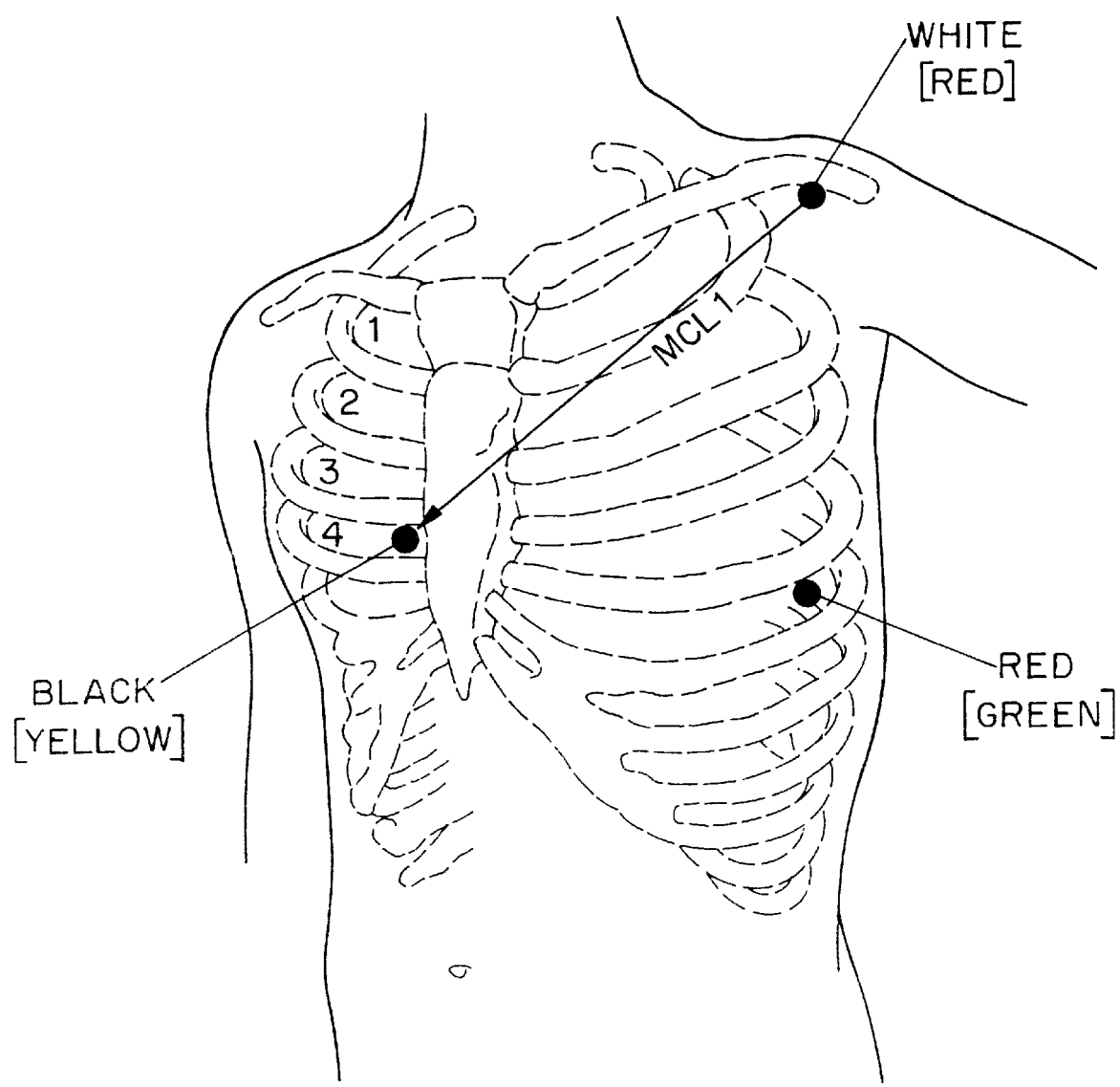
FIG. 16 shows the placement of a 3-lead electrode leadset on a patient's torso.
Figure 17:
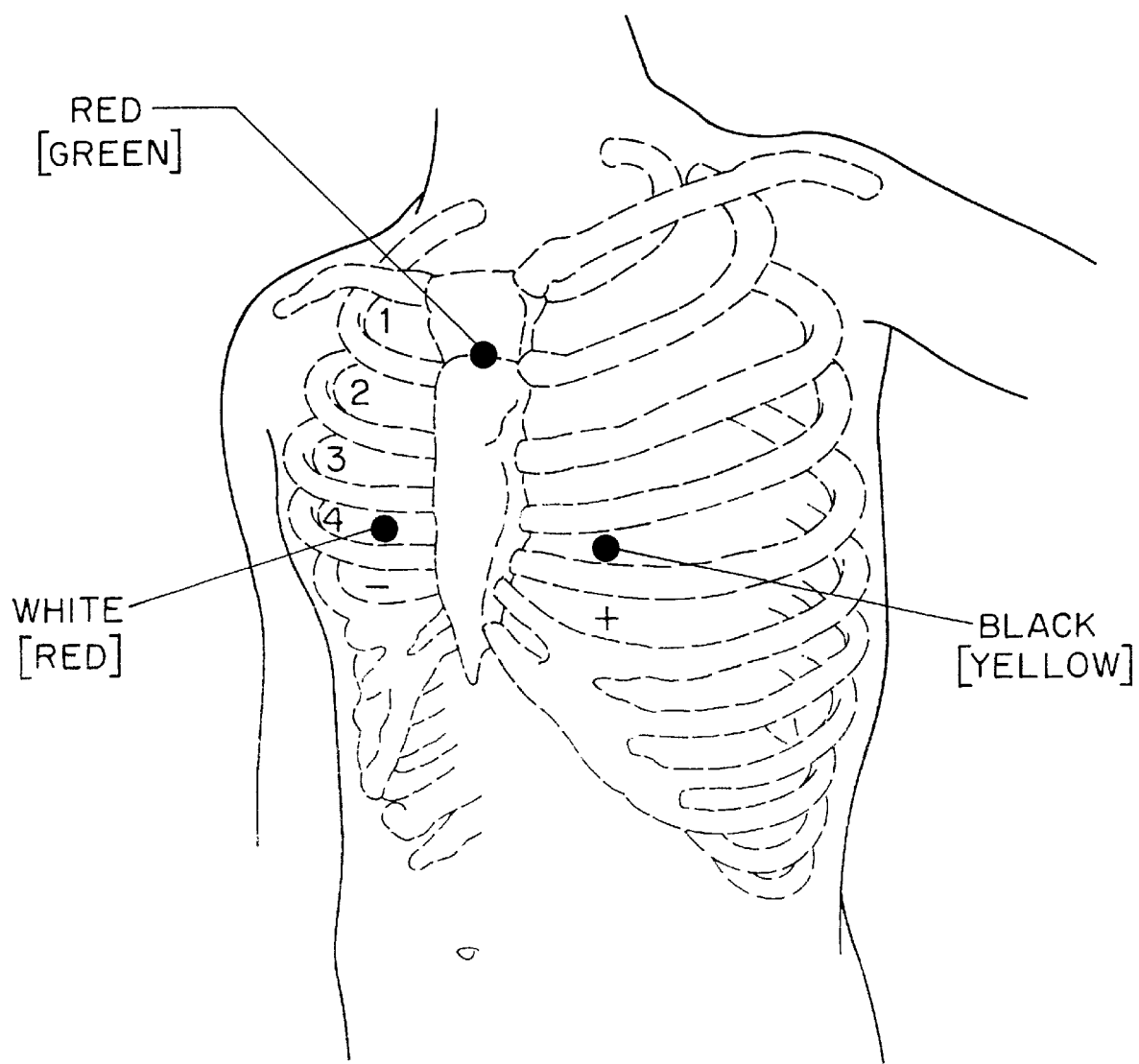
FIG. 17 shows the placement of a 3-lead electrode leadset on a patient's torso for paced patients.
Figure 18:
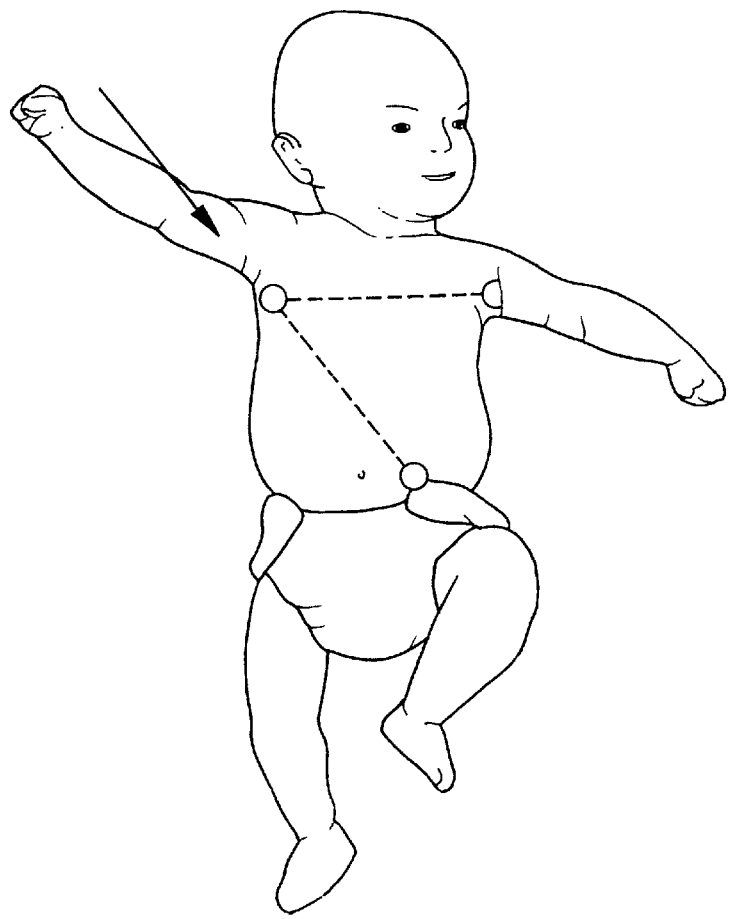
FIG. 18 shows the placement of a 3-lead electrode leadset on an infant.
Figure 19:
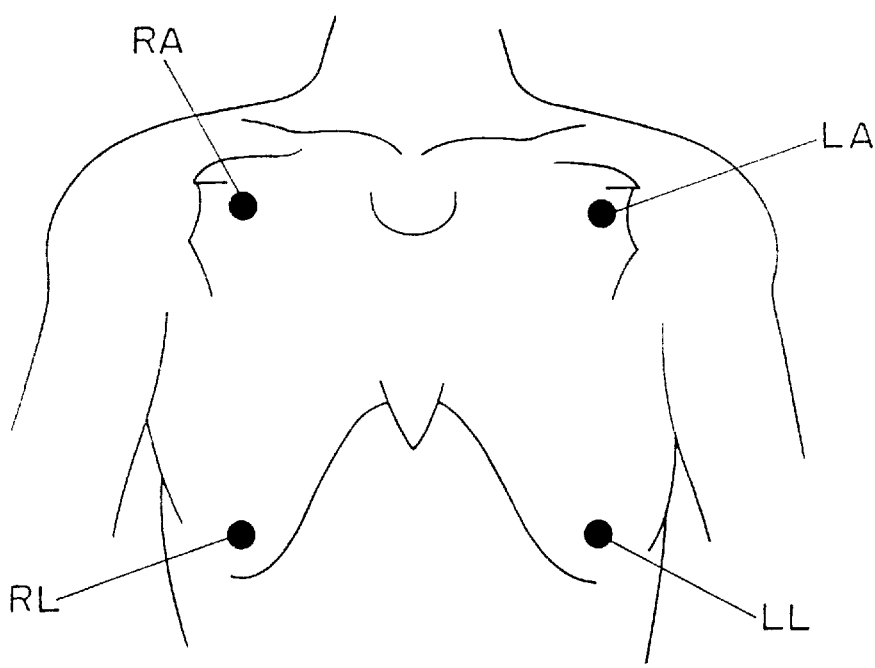
FIG. 19 shows the placement of a 4-lead electrode leadset on a patient's torso.
Figure 20:
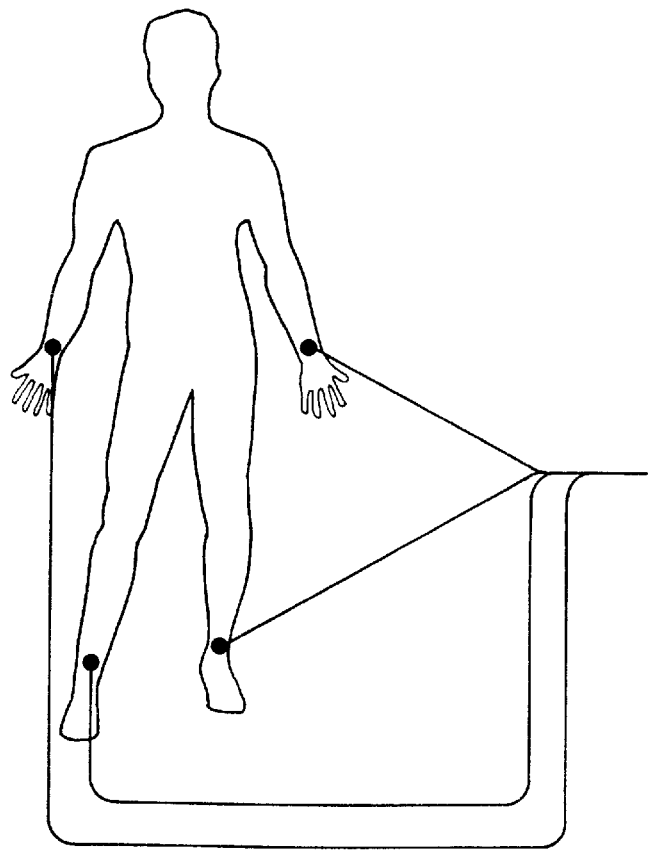
FIG. 20 shows the placement of a 4-lead electrode leadset on a patient's limbs.
Figure 22:
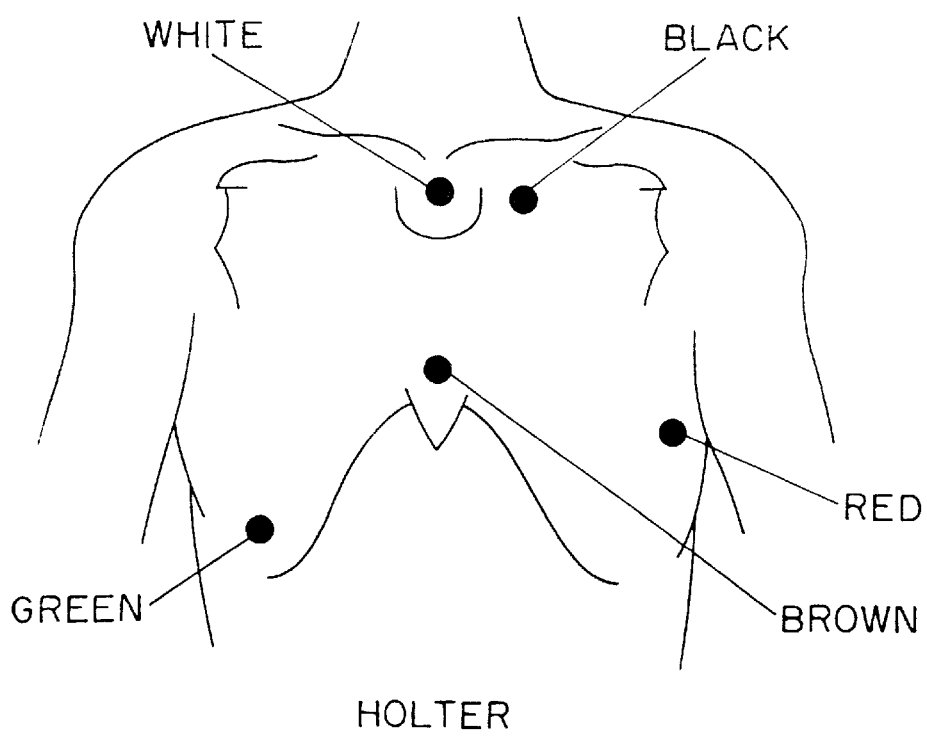
FIG. 22 shows the placement of a 5-lead electrode leadset on a patient's torso for holter recording.
Figure 21:
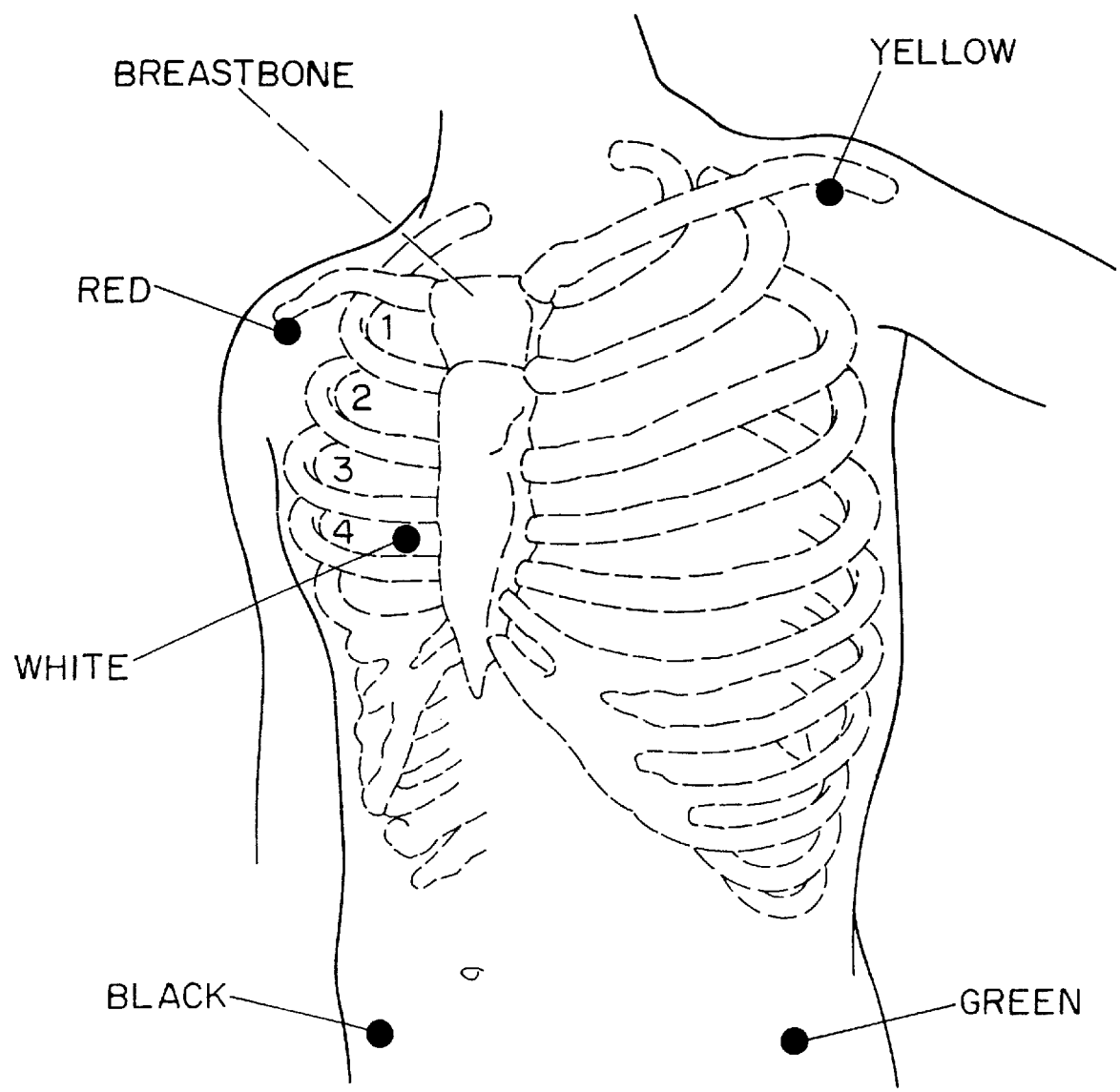
FIG. 21 shows the placement of a 5-lead electrode leadset on a patient's torso for monitoring.
Figure 23:
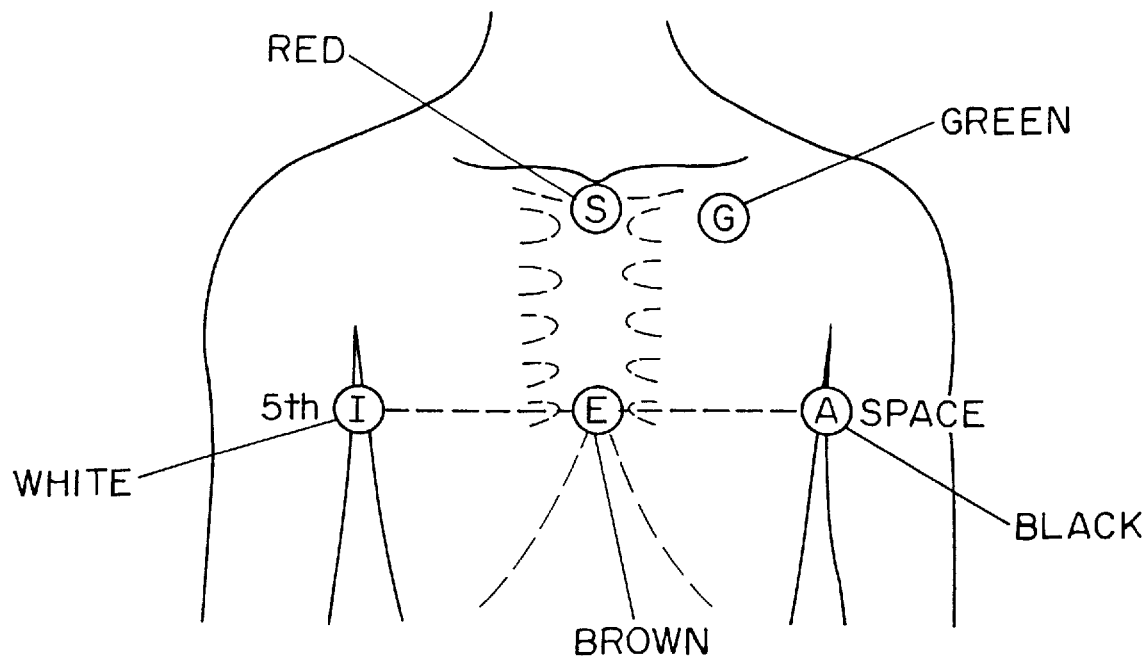
FIG. 23 shows the placement of a 5-lead electrode leadset on a patient according to the EASI leadset.
Figure 24:
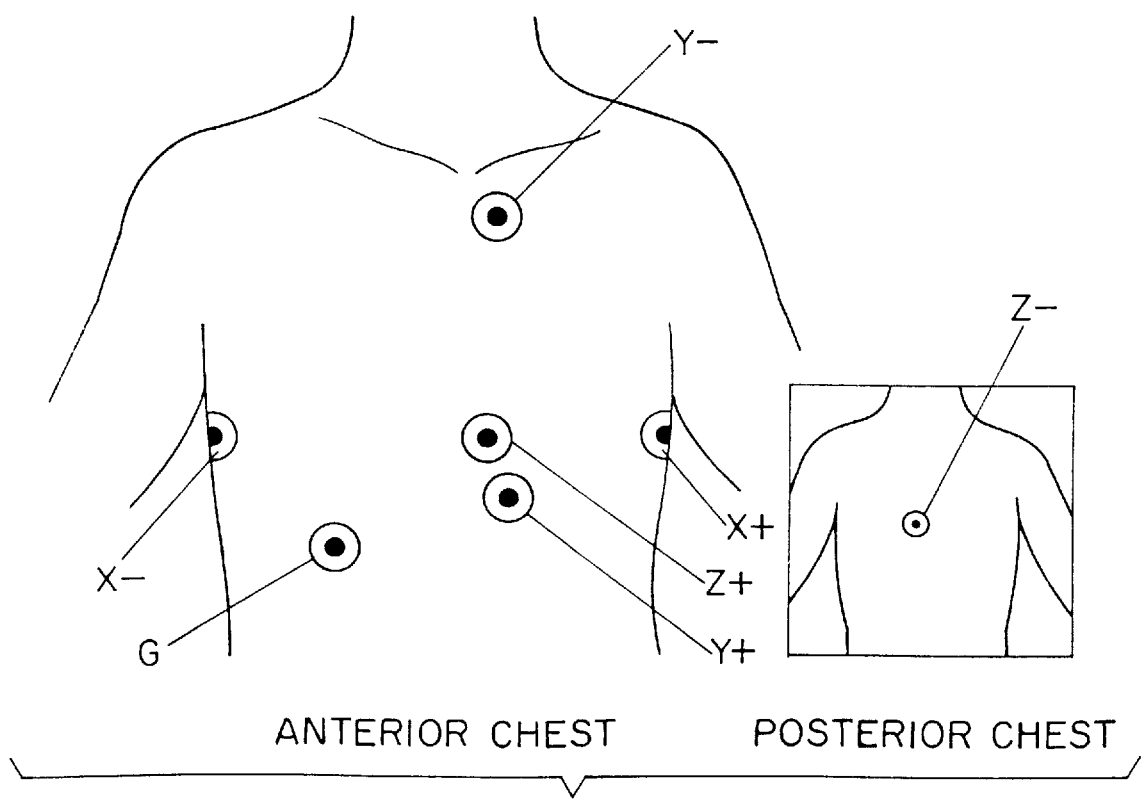
FIG. 24 shows the placement of a 7-lead electrode leadset on a patient's torso for late potential analysis.
Figure 25:
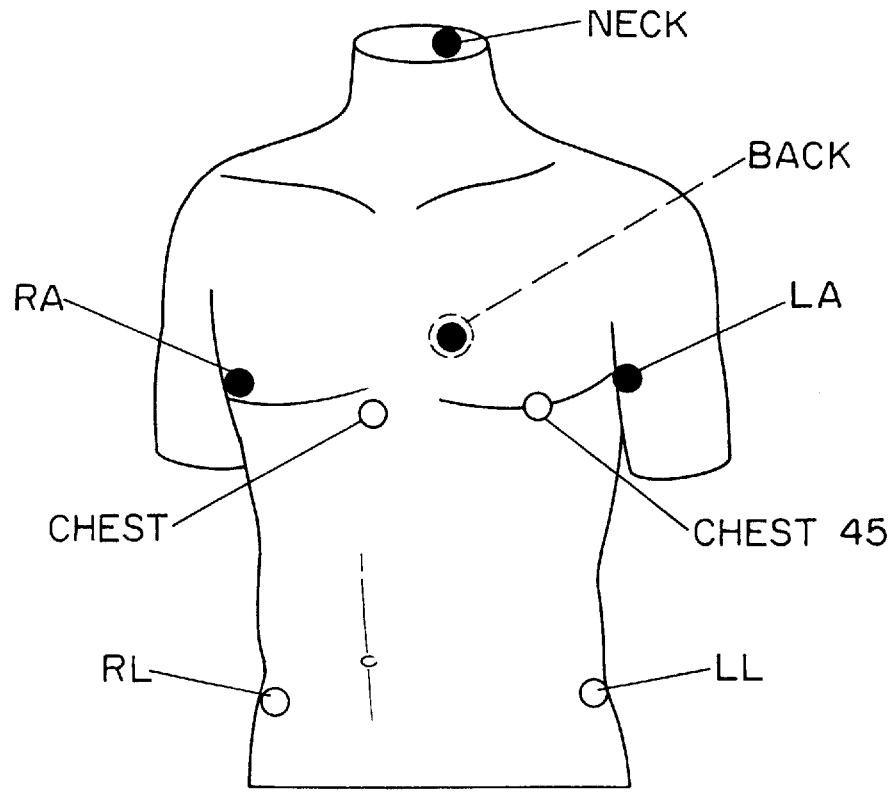
FIG. 25 shows the placement of an 8-lead electrode leadset on a patient's torso according to Frank.
Figure 26:
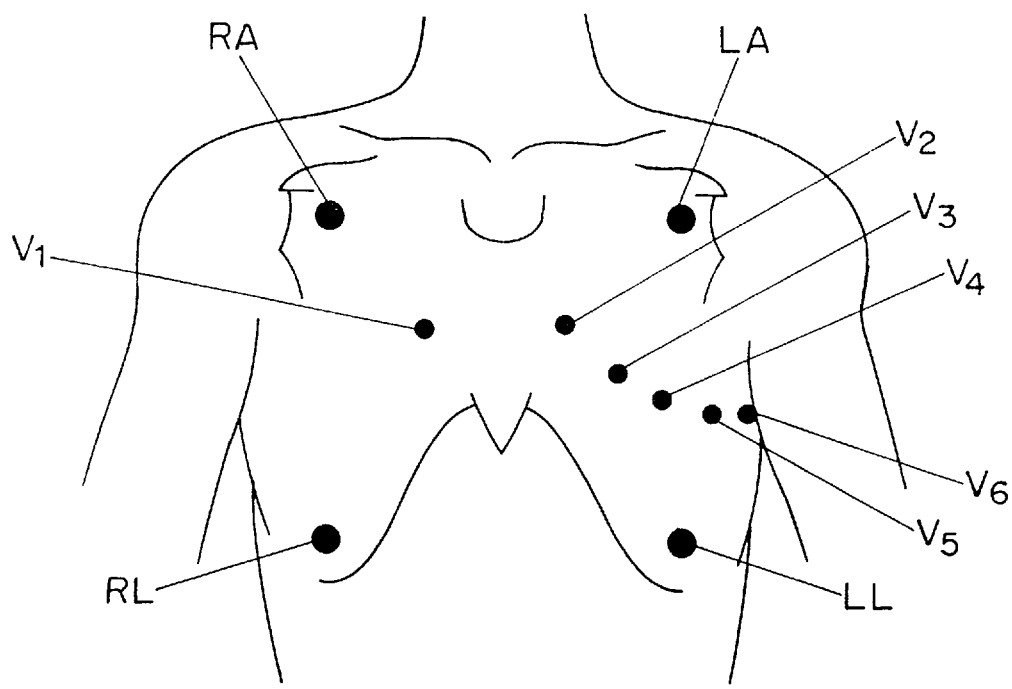
FIG. 26 shows the placement of a 10-lead electrode leadset on a patient's torso to get true 12-lead ECG (RA and LA may be placed on arms, RL and LL further down on legs).

The invention is not limited to the systems and methods illustrated in the drawings and described above. Modifications and variations are possible within the inventive concept. For example, in addition to the electrode leadsets discussed above, the following leadsets may be used: the 3-lead electrode leadsets of FIGS. 16, 17, and 18, the 4-lead electrode leadsets of Figs. 19 and 20, the 5-lead electrode leadsets of FIGS. 21, 22, and 23 (the EASI leadset and algorithm of FIG. 23 are covered by U.S. Pat. No. 4,850,370, Issued Jul. 25, 1989), the 7-lead electrode leadset of FIG. 24, the 8-lead electrode leadset of FIG. 25 according to Frank, and the 10-lead electrode leadset of FIG. 26. In addition, body surface mapping (normally with 48 electrodes) may be applied to the invention. Accordingly, the disclosure should not be construed as limiting the scope of the following claims, which specifically define the invention.

What is claimed is:

1. A system for monitoring, analyzing, and/or diagnosing the cardiac activity of a patient, comprising:

plurality of electrodes positioned at a respective plurality of locations on the patient for directing a respective plurality of electrical signals from the patient;

ECG data production means connected to the plurality of electrodes for acquiring said plurality of electrical signals directed by the plurality of electrodes and for producing ECG data in response to the acquired electrical signals;

display means connected to the ECG data production means for displaying a graphic depiction of at least part of the patient, the location, on the graphic depiction of at least part of the patient, of each of said plurality of electrodes, and a status of each of said electrical signals directed from said plurality of electrodes, wherein the status of each of said electrical signals directed from each of said plurality of electrodes includes at least one condition in which the electrical signal has a value such that the ECG production means is unable to produce a valid ECG signal in response thereto.

2. The system of claim 1, wherein said display means includes a plurality of electrode status indicators, each of said plurality of electrode status indicators being disposed on the graphical depiction of at least part of the patient at a position substantially corresponding to one of said plurality of locations on the patient at which one of said plurality of electrodes is positioned.

3. The system of claim 2, wherein said display means includes a plurality of electrode status annunciators, each of said plurality of electrode status annunciators being alphanumeric indicators and corresponding to at least one of said electrode status indicators.

4. The system of claim 3, wherein the status of each of said plurality of electrical signals directed from each of the plurality of electrodes further includes a first condition in which the electrical signal is out of the acquisition range of the ECG production means, a second condition in which the electrical signal is too noisy for the ECG production means to produce a proper ECG signal in response thereto, a third condition in which the electrical signal exhibits baseline drift, and a fourth condition in which the signal exhibits a spike, wherein each of said plurality of electrode status indicators produces a graphic output when the electrical signal corresponding thereto is in one of the first, second, third, or fourth conditions and each of said electrode status annunciators indicates which of said conditions the corresponding electrical signal is in.

5. The system of claim 4, wherein each of said electrode status annunciators is adapted to selectively display an impedance value of at least one of said plurality of electrodes.

6. The system of claim 2, wherein the status of each of said plurality of electrical signals directed from each of the plurality of electrodes further includes a first condition in which the electrical signal is out of the acquisition range of the ECG production means and a second condition in which the electrical signal is too noisy for the ECG production means to produce a proper ECG signal in response thereto, wherein each of said plurality of electrode status indicators produces a first graphic output when the electrical signal corresponding thereto is in the first condition and each of said electrode status indicators produces a second graphic output when the electrical signal corresponding thereto is in the second condition.

7. The system of claim 2, wherein said display means comprises a cathode ray tube.

8. The system of claim 2, wherein said display means comprises a plasma display.

9. The system of claim 2, wherein said display means comprises a liquid crystal display.

10. The system of claim 2, wherein said display means comprises an electroluminescent display.

11. The system of claim 1, wherein said display means includes a translucent overlay having a graphical depiction of at least part of the patient and a plurality of light production means disposed behind the translucent overlay, each of said plurality of light production means being disposed behind the transparent overlay at a position substantially corresponding to one of said plurality of locations on the patient at which one of said plurality of electrodes is positioned.

12. The system of claim 11, wherein each of said plurality of light production means is a light emitting diode.

13. The system of claim 12, wherein the status of each of said plurality of electrical signals directed from each of the plurality of electrodes further includes a first condition in which the electrical signal is out of the acquisition range of the ECG production means and a second condition in which the electrical signal is too noisy for the ECG production means to produce a proper ECG signal in response thereto, wherein each of said light emitting diodes produces a first light output when the electrical signal corresponding thereto is in the first condition and each of said light emitting diodes produces a second light output when the electrical signal corresponding thereto is in the second condition.

14. A method for monitoring, analyzing, and/or diagnosing the cardiac activity of a patient, comprising:

positioning a plurality of electrodes at a respective plurality of locations on the patient for directing a respective plurality of electrical signals from the patient;

acquiring said plurality of electrical signals by connecting ECG data production means to the plurality of electrodes;

producing ECG data in response to the acquired electrical signals; and displaying on display means connected to the ECG production means the location, on the patient, of each of said plurality of electrodes and a status of each of said electrical signals, wherein the status of each of said electrical signal has a value such that the ECG data production means is unable to produce a valid ECG signal in response thereto.

15. The method of claim 14, wherein said display means includes a graphical depiction of at least part of the patient and a plurality of electrode status indicators, each of said plurality of electrode status indicators being disposed on the graphical depiction of at least part of the patient at a position substantially corresponding to one of said plurality of locations on the patient at which one of said plurality of electrodes is positioned.

16. The method of claim 15, wherein said display means includes a plurality of electrode status annunciators, each of said plurality of electrode status annunciators being alphanumeric indicators and corresponding to at least one of said electrode status indicators.

17. The method of claim 16, wherein the status of each of said plurality of electrical signals directed from each of the plurality of electrodes further includes a first condition in which the electrical signal is out of the acquisition range of the ECG production means, a second condition in which the electrical signal is too noisy for the ECG production means to produce a proper ECG signal in response thereto, a third condition in which the electrical signal exhibits baseline drift, and a fourth condition in which the signal exhibits a spike, wherein each of said plurality of electrode status indicators produces a graphic output when the electrical signal corresponding thereto is in one of the first, second, third, or fourth conditions and each of said electrode status annunciators indicates which of said conditions the corresponding electrical signal is in.

18. The method of claim 15, wherein the status of each of said plurality of electrical signals further includes a first condition in which the electrical signal is out of the acquisition range of the ECG production means and a second condition in which the electrical signal is too noisy for the ECG production means to produce a proper ECG signal in response thereto, wherein each of said plurality of electrode status indicators produces a first graphic output when the electrical signal corresponding thereto is in the first condition and each of said electrode status indicators produces a second graphic output when the electrical signal corresponding thereto is in the second condition.

19. The method of claim 14, wherein said display means includes a translucent overlay having a graphical depiction of at least part of the patient and a plurality of light production means disposed behind the translucent overlay, each of said plurality of light production means being disposed behind the transparent overlay at a position substantially corresponding to one of said plurality of locations on the patient at which one of said plurality of electrodes is positioned.

20. The method of claim 19, wherein each of said plurality of light production means is a light emitting diode.

21. The method of claim 20, wherein the status of each of said plurality of electrical signals further includes a first condition in which the electrical signal is out of the acquisition range of the ECG production means and a second condition in which the electrical signal is too noisy for the ECG production means to produce a proper ECG signal in response thereto, wherein each of said light emitting diodes produces a steady light output when the electrical signal corresponding thereto is in the first condition and each of said light emitting diodes produces a blinking light output when the electrical signal corresponding thereto is in the second condition.

* * * * *